US008431160B2

(12) United States Patent
O'Hagan et al.

(10) Patent No.: US 8,431,160 B2
(45) Date of Patent: Apr. 30, 2013

(54) MICROPARTICLES CONTAINING BIODEGRADABLE POLYMER AND CATIONIC POLYSACCHARIDE FOR USE IN IMMUNOGENIC COMPOSITIONS

(75) Inventors: Derek O'Hagan, Siena (IT); Manmohan Singh, San Ramon, CA (US); Janet Wendorf, Redwood City, CA (US); Jina Kazzaz, San Rafael, CA (US); Padma Malyala, Santa Clara, CA (US)

(73) Assignee: Novartis AG, Basel (CH)

( * ) Notice: Subject to any disclaimer, the term of this patent is extended or adjusted under 35 U.S.C. 154(b) by 1308 days.

(21) Appl. No.: 11/710,250

(22) Filed: Feb. 24, 2007

(65) Prior Publication Data

US 2009/0169636 A1 Jul. 2, 2009

Related U.S. Application Data

(60) Provisional application No. 60/776,757, filed on Feb. 24, 2006.

(51) Int. Cl.
| | | |
|---|---|---|
| *A61K 9/14* | (2006.01) | |
| *A61K 39/00* | (2006.01) | |
| *A61K 39/39* | (2006.01) | |
| *A61K 39/12* | (2006.01) | |
| *A61K 39/02* | (2006.01) | |
| *A61K 39/002* | (2006.01) | |
| *A61K 39/21* | (2006.01) | |
| *A61K 39/29* | (2006.01) | |
| *A61K 39/145* | (2006.01) | |
| *A61K 39/10* | (2006.01) | |
| *A61K 39/05* | (2006.01) | |
| *A61K 39/08* | (2006.01) | |
| *A61P 37/04* | (2006.01) | |

(52) U.S. Cl.
USPC .............. 424/499; 424/184.1; 424/193.1; 424/204.1; 424/206.1; 424/227.1; 424/228.1; 424/234.1; 424/254.1; 424/265.1; 424/274.1; 424/276.1; 424/277.1

(58) Field of Classification Search ............ None
See application file for complete search history.

(56) References Cited

U.S. PATENT DOCUMENTS

| | | | |
|---|---|---|---|
| 6,514,522 B2 * | 2/2003 | Domb ..................... | 424/443 |
| 6,884,435 B1 | 4/2005 | O'Hagan et al. ........... | 424/489 |
| 2003/0049298 A1 | 3/2003 | O'Hagan et al. ........... | 424/418 |
| 2004/0101537 A1 | 5/2004 | O'Hagan et al. ........ | 424/249.1 |
| 2005/0106178 A1 | 5/2005 | O'Hagan ................. | 424/209.1 |
| 2005/0244505 A1 * | 11/2005 | Higbee et al. ............ | 424/489 |

FOREIGN PATENT DOCUMENTS

| | | |
|---|---|---|
| WO | WO 98/33487 | 8/1998 |
| WO | WO 99/27960 | 6/1999 |
| WO | WO 00/06123 | 2/2000 |
| WO | 0056362 | 9/2000 |
| WO | WO 00/78924 A1 | 12/2000 |
| WO | WO 01/36599 | 5/2001 |
| WO | WO 03/086454 A1 | 10/2003 |
| WO | 2005072088 | 8/2005 |
| WO | WO 2007/013893 A2 | 2/2007 |

OTHER PUBLICATIONS

Single, 53, 2001, p. 1047, J. of Pharmacy and pharmacology.*
Vila, J.78, 2002 p. 15, Controlled Release.*
M.N.V. Ravi Kumar et al., "Preparation and Characterization of Cationic PLGA Nanospheres as DNA Carriers", *Biomaterials*, vol. 25, No. 10, May 2004, pp. 1771-1777.
J.R. Wendorf et al., "Nanoparticles and Microparticles as Vaccine Adjuvants," Nanoparticulates as Drug Carriers, 1$^{st}$ Ed. Sep. 29, 2006, World Scientific Pub. Inc., pp. 675-696.
T. Nagamoto et al., "Novel chitosan particles and chitosan-coated emulsions inducing immune response via intranasal vaccine delivery," *Pharm Res* 21, 2004, pp. 671-674.
A. Vila et al., "Design of biodegradable particles for protein delivery," *J Control Release*. 78(1-3), 2002, pp. 15-24.
A. Vila et al., "Low molecular weight chitosan nanoparticles as new carriers for nasal vaccine delivery in mice," *European Journal of Pharmaceutics and Biopharmaceutics* 57, 2004, pp. 123-131.
A. Bacon et al. "Carbohydrate biopolymers enhance antibody responses to mucosally delivered vaccine antigens." *Infect Immun.*, 68, 10, 2000, pp. 5764-5770.
A.K. Singla et al., "Chitosan: some pharmaceutical and biological aspects—an update." *J. Pharm. Pharmacol.* 53, 2001, pp. 1047-1067.
P. Calvo et al. "Development of positively charged colloidal drug carriers: Chitosan coated polyester nanocapsules and submicron-emulsions." *Colloid Polym Sci* 275, 1997, pp. 46-53.
E. A. McNeela et al., "Intranasal immunization with genetically detoxified diphtheria toxin induces T cell responses in humans: enhancement of TH2 responses and toxin-neutralizing antibodies by formulation with chitosan." *Vaccine*, vol. 22, 2004, pp. 909-914.
L. Illum et al. "Chitosan as a novel nasal delivery system for vaccines," *Adv Drug Deliv. Rev.*, 51, 2001, pp. 81-96.
K. Roy et al., "Oral delivery with Chitosan—DNA nanoparticles generate immunologic protection in a murine model of peanut allergy," *Nat. Med.* 5, 1999, pp. 387-391.
M. Bivas-Benita et al. Pulmonary delivery of chitosan-DNA nanoparticles enhances the immunogenicity of a DNA vaccine encoding HLA-A*0201-restricted T-cell epitopes of *Mycobacterium tuberculosis. Vaccine* 22, 2004, pp. 1609-1615.

(Continued)

*Primary Examiner* — David J Blanchard
*Assistant Examiner* — Thurman Wheeler
(74) *Attorney, Agent, or Firm* — Helen Lee; David B. Bonham

(57) ABSTRACT

Immunogenic compositions are described herein which comprise microparticles that further comprise a biodegradable polymer. The microparticle compositions also comprise a cationic polysaccharide and an immunological species selected from an antigen, an immunological adjuvant and a combination thereof. Also described are methods of making such compositions and methods of administering such compositions. Methods of modulating the release rate of immunological species from microparticles are also described. These methods comprise varying the ratio of the cationic polysaccharide relative to the biodegradable polymer within the microparticles.

65 Claims, 4 Drawing Sheets

OTHER PUBLICATIONS

Prochazkova S. "Quantitative determination of chitosans by ninhydrin" *Carbohydrate Polymers* 38, 1999, pp. 115-122.

Singh M. et al. "Anionic Microparticles are a Potent Delivery System for Recombinant Antigens from *Neisseria meningitidis* Serotype B", *J. Pharm. Sci.* 93, 2, 2004, pp. 273-282.

Singh, M., et al., "Cationic microparticles: A potent delivery system for DNA vaccines", *Proc. Natl. Acad. Sci. USA* 97, 2, 2000, pp. 811-816.

I. Jabbal-Gill et al., "Stimulation of mucosal and systemic antibody responses against *Bordetella pertussis* filamentous haemagglutinin and recombinant pertussis toxin after nasal administration with chitosan in mice." Vaccine. 16, 1998, pp. 2039-2046.

K. Dillen et al., "Physical characterization of chitosan-coated PLGA nano-particles prepared by solvent evaporation", Autumn Meeting of the Belgian-Dutch Biopharmaceutical Society, Dec. 13, 2002, 2 pages.

\* cited by examiner

MICROPARTICLES CONTAINING BIODEGRADABLE POLYMER AND CATIONIC POLYSACCHARIDE FOR USE IN IMMUNOGENIC COMPOSITIONS

STATEMENT OF RELATED APPLICATION

This application claims the benefit of U.S. provisional patent application No. 60/776,757 filed Feb. 24, 2006, which is incorporated herein by reference in its entirety.

BACKGROUND

Particulate carriers have been used with adsorbed or entrapped antigens in attempts to elicit adequate immune responses. Such carriers present multiple copies of a selected antigen to the immune system and are believed to promote trapping and retention of antigens in local lymph nodes. The particles can be phagocytosed by macrophages and can enhance antigen presentation through cytokine release.

For example, commonly owned International patent application WO 98/33487 and co-pending U.S. Patent Application Publication No. 2003/0049298 describe the use of antigen-adsorbed and antigen-encapsulated microparticles to stimulate immunological responses, including cell-mediated immunological responses, as well as methods of making the microparticles. Polymers used to form the microparticles include poly(lactide) and poly(lactide-co-glycolide) (PLG).

Commonly owned International patent applications WO 00/06123 and WO 01/36599 and U.S. Pat. No. 6,884,435 disclose methods of making microparticles having adsorbed macromolecules, including polynucleotides and polypeptide antigens. The microparticles comprise, for example, a polymer such as a poly(alpha-hydroxy acid) (e.g., PLG, a polyhydroxy butyric acid, a polycaprolactone, a polyorthoester, a polyanhydride, and the like) and are formed using, for example, cationic, anionic or nonionic detergents. Microparticles containing anionic detergents, such as PLG microparticles containing sodium dodecyl sulfate (SDS), are described for the use of positively charged macromolecules, such as polypeptides. Microparticles containing cationic detergents, such as PLG microparticles with CTAB (also known as cetrimide or cetyl trimethyl ammonium bromide), are described for the use of negatively charged macromolecules, such as DNA. The use of such microparticles to stimulate immunological responses, including cell-mediated immunological responses, is also disclosed.

SUMMARY OF THE INVENTION

In one aspect, the present invention provides immunogenic compositions which comprise microparticles that further comprise a biodegradable polymer. The microparticle compositions also comprise a cationic polysaccharide and an immunological species selected from an antigen, an immunological adjuvant and a combination thereof.

In some embodiments, the immunological species are adsorbed to the microparticles. In these embodiments, the weight ratio of the cationic polysaccharide to the biodegradable polymer may vary, ranging, for example, from 0.0005:1 to 0.001:1 to 0.0025:1 to 0.005:1 to 0.01:1 to 0.025:1 to 0.05:1, among other ratios. The weight ratio of the immunological species to the biodegradable polymer may also vary, ranging, for example, from 0.0005:1 to 0.001:1 to 0.0025:1 to 0.005:1 to 0.01:1 to 0.025:1 to 0.05:1, among other ratios.

In some embodiments, the immunological species is entrapped within the microparticles. In these embodiments, the weight ratio of the cationic polysaccharide to the biodegradable polymer may vary, ranging, for example, from 0.00005:1 to 0.0001:1 to 0.00025:1 to 0.0005:1 to 0.001:1 to 0.0025:1 to 0.005:1, among other ratios. The weight ratio of the cationic polysaccharide to said immunological species may also vary, ranging, for example, from 0.0001:1 to 0.00025:1 to 0.0005:1 to 0.001:1 to 0.0025:1 to 0.005:1 to 0.01:1, among other ratios.

The mean particle diameter of the microparticles may vary broadly, ranging for example, from 0.1 to 50 microns, more typically from 0.5 to 10 microns in D(v,0.5) particle size.

Where the compositions of the invention comprise two antigens, two immunological adjuvants, or one antigen and one immunological adjuvant, they may be, for example, (a) both adsorbed to the same population of microparticles, (b) each adsorbed to separate populations of microparticles, (c) one adsorbed to or entrapped within microparticles and the other in solution, (d) one adsorbed to microparticles and the other entrapped within the same population of microparticles, (e) one adsorbed to a first population of microparticles and the other entrapped within the a second population of microparticles, (f) both entrapped within the same population of microparticles, (g) each entrapped within separate populations of microparticles, and so forth.

In certain embodiments, the cationic polysaccharide comprises an amine-substituted cationic polysaccharide, for example, one comprising D-glucosamine monomer units, among others. Specific examples of cationic polysaccharides include those that comprise a polymer chain that in turn comprises randomly distributed β-(1-4)-linked D-glucosamine and N-acetyl-D-glucosamine monomer units, for example, chitosan, among others.

In certain embodiments, the immunogenic compositions of the invention comprise a synthetic biodegradable polymer, for example, selected from poly(α-hydroxy acids), polyhydroxy butyric acids, polylactones including polycaprolactones, polydioxanones and polyvalerolactone, polyorthoesters, polyanhydrides, polycyanoacrylates, tyrosine-derived polycarbonates or polyester-amides, and combinations thereof, among others. In certain embodiments, the microparticles are formed from poly(α-hydroxy acids), such as a poly(lactides) ("PLA"), copolymers of lactide and glycolide, such as a poly(D,L-lactide-co-glycolide) ("PLG"), and copolymers of D,L-lactide and caprolactone, among others. Poly(D,L-lactide-co-glycolide) polymers include those having a lactide/glycolide molar ratio ranging, for example, from 20:80 to 25:75 to 40:60 to 45:55 to 55:45 to 60:40 to 75:25 to 80:20, and having a molecular weight ranging, for example, from 5,000 to 10,000 to 20,000 to 40,000 to 50,000 to 70,000 to 100,000 to 200,000 Daltons, among others.

Antigens may be elected, for example, from polypeptide-containing antigens, polynucleotide-containing antigens, and saccharide-containing antigens. Antigens may be derived, for example, from tumor cells and pathogenic organisms such as viruses, bacteria, fungi and parasites.

Immunological adjuvants may be selected, for example, from negatively charged immunological adjuvants such as CpG oligonucleotides as well as MPL analogs, among others.

In certain embodiments, the immunogenic compositions of the invention are lyophilized compositions. Such lyophilized compositions may comprise, for example, 90 wt % biodegradable polymer or more.

In other aspects, the present invention provides methods of producing microparticle compositions such as the foregoing. The cationic polysaccharide may play different roles in the production processes, depending upon the desired product.

For example, in some embodiments, the cationic polysaccharide may be used as a complexing agent for the immunological species, allowing the immunological species to be readily entrapped within microparticles. Hence, in these embodiments, the chitosan acts as a capturing agent. These embodiments include methods of producing microparticle compositions that comprise the following steps: (a) emulsifying an organic phase comprising a biodegradable polymer and an organic solvent with a first aqueous phase comprising water and a complex of a cationic polysaccharide and a immunological species, thereby forming a water-in-oil emulsion; (b) emulsifying a second aqueous phase comprising a surfactant and water with the emulsion formed in step (a) to form a water-in-oil-in-water emulsion; and (c) removing the organic solvent from the water-in-oil-in-water emulsion, thereby providing a suspension of microparticles with entrapped immunological species and cationic polysaccharide.

In other embodiments, the cationic polysaccharide may be used during emulsion-based processing to stabilize the dispersed oil phase, which is ultimately transformed into solid microparticles (upon solvent evaporation). These embodiments include methods of producing microparticle compositions that comprise the following steps: (a) providing an emulsion comprising water, organic solvent, a biodegradable polymer and a cationic polysaccharide; (b) removing the organic solvent from the emulsion to form microparticles; and (c) adsorbing an immunological species to the microparticles. In certain instances, the emulsion may be a water-in-oil-in-water emulsion which is formed by a process that comprises (a) emulsifying an organic phase comprising the biodegradable polymer and the organic solvent with a first aqueous phase comprising water, thereby forming a water-in-oil emulsion; and (b) emulsifying a second aqueous phase comprising the cationic polysaccharide and water with the emulsion formed in step (a) to form the water-in-oil-in-water emulsion.

In these embodiments, it is believed that a substantial amount of the cationic polymer is located at the microparticle surfaces. This is evidenced, for example, by the fact that the resulting microparticles generally have positive zeta potentials, for example, ranging from +25 to +100 mV at pH ranging from 5.0 to 6.5 prior to adsorption of any immunological species. Moreover, it is believed that the positive charge of the microparticles improves the ability of the microparticles to remain in suspension when suspended in aqueous media. Moreover, it is believed that the positive charge of the microparticles improves the ability of the microparticles to adsorb negatively charged species. Hence, in these embodiments, the chitosan acts as a binding agent.

Still other aspects of the invention are directed to methods of modulating the release rate of immunological species from microparticle compositions such as the foregoing, which comprise varying the ratio of the cationic polysaccharide surfactant relative to the biodegradable polymer within the microparticles. For example, the present inventors have found that the release rate of certain immunological species is decreased by increasing the ratio of the cationic polysaccharide surfactant relative to the biodegradable polymer within the microparticles.

Other embodiments of the invention are directed to methods of delivering immunological species to a host animal (e.g., for immunization), which comprises administering to the host animal any of the immunogenic compositions described herein. The host animal is preferably a vertebrate animal, more preferably a mammal, and even more preferably a human.

Delivery of the immunogenic compositions of the invention may be performed by any known method, including direct injection (e.g., subcutaneously, intravenously, intramuscularly or intraperitoneally, etc).

In further aspects, the present invention provides kits comprising the compositions of the invention.

Advantages of the present invention are that, relative to other common cationic species, such as CTAB, cationic polysaccharides, such as chitosan, offer the potential for one or more of the following, among others: (a) lower toxicity, (b) higher charge densities, particularly where cationic polysaccharides having charges along the length of the polymer are used, (c) where used as a complexing agent, improved encapsulation, and (d) where used as a particle stabilizer, (i) better association of the cationic species with the microparticle surfaces, (ii) increased adsorption of immunological species, and (iii) sustained release of adsorbed immunological species. These and other embodiments, aspects and advantages of the present invention will become more readily apparent to those of ordinary skill in the art in view of the disclosure herein.

DETAILED DESCRIPTION OF THE INVENTION

Figure 1:
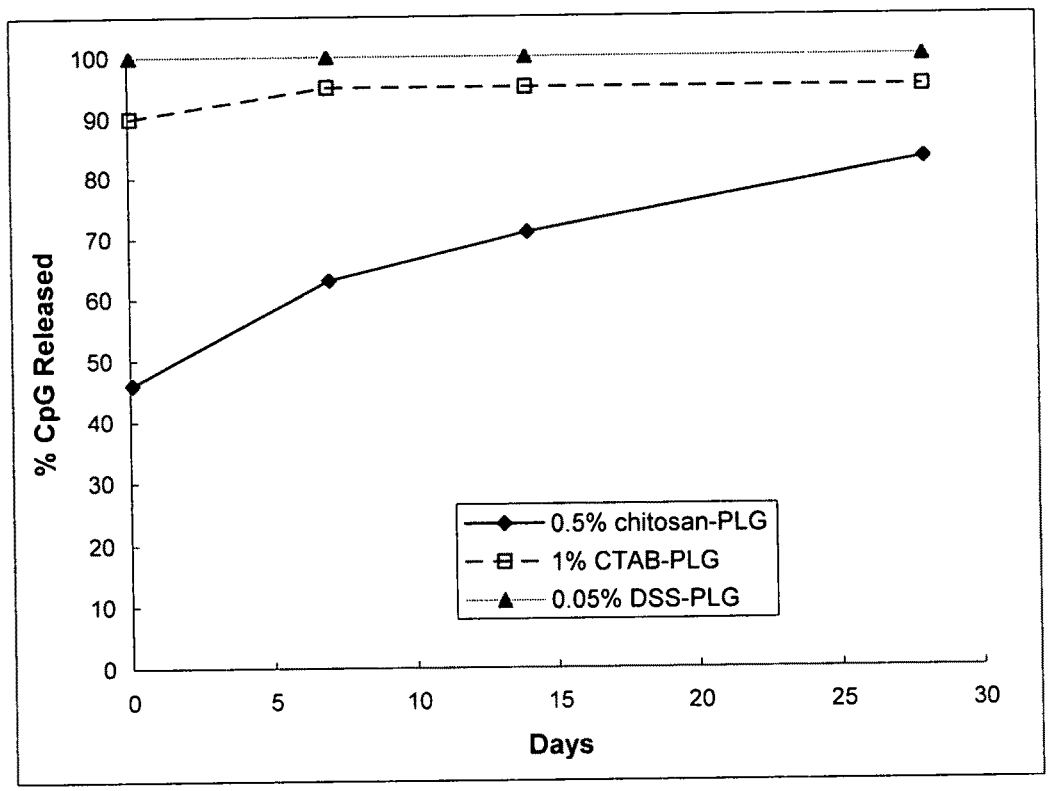
FIG. 1 is a plot of CpG release over 28 days for varying particle types having an initial target load of 1% for adsorbed CpG wt/wt relative to PLG.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); Weir, D. M., *Handbook of Experimental Immunology,* Vols. I-IV, 5th ed. (Blackwell Publishers, 1996); Sambrook, J. et al., *Molecular Cloning: A Laboratory Manual,* 3rd ed. (Cold Spring Harbor Laboratory Press, 2001); Ausubel, F. M. et al., *Short Protocols In Molecular Biology,* 5th ed. (Current Protocols, 2002); *Handbook of Surface and Colloidal Chemistry* (Birdi, K. S., ed, CRC Press, 1997) and *Seymour/Carraher's Polymer Chemistry,* 5th ed. (Marcel Dekker Inc., 2000).

All publications, patents and patent applications cited herein, whether supra or infra, are hereby incorporated by reference in their entirety.

As used in this specification and any appended claims, the singular forms "a," "an" and "the" include plural references unless the content clearly dictates otherwise. Thus, for example, the term "microparticle" refers to one or more microparticles, and the like.

Unless stated otherwise or unless the context clearly dictates otherwise, all percentages and ratios herein are given on a weight basis.

A. DEFINITIONS

In describing the present invention, the following terms will be employed, and are intended to be defined as indicated below.

The term "microparticle" as used herein, refers to a particle of about 10 nm to about 150 µm in diameter, more typically about 200 nm to about 30 µm in diameter, and even more typically about 500 nm to about 10 µm in diameter. The microparticles of the present invention may aggregate into larger masses under some circumstances, such as lyophilization. The microparticle will generally be of a diameter that permits parenteral or mucosal administration without occluding needles and capillaries. Microparticle size is readily determined by techniques well known in the art, such as photon correlation spectroscopy, laser diffractometry and/or scanning electron microscopy. The term "particle" may also be used to denote a microparticle as defined herein.

Particle size can be determined (measured) using methods available in the art. For example, particle size can be determined using photon correlation spectroscopy, dynamic light scattering or quasi-elastic light scattering. These methods are based on the correlation of particle size with diffusion properties of particles obtained from Brownian motion measurements. Brownian motion is the random movement of the particles due to bombardment by the solvent molecules that surround the particles. The larger the particle, the more slowly the Brownian motion will be. Velocity is defined by the translational diffusion coefficient (D). The value measured refers to how a particle moves within a liquid (hydrodynamic diameter). The diameter that is obtained is the diameter of a sphere that has the same translational diffusion coefficient as the particle.

Particle size can also be determined using static light scattering, which measures the intensity of light scattered by particles in a solution at a single time. Static light scattering measures light intensity as a function of scattering angle and solute concentration. Particles passing though a light source, for example, a laser beam, scatter light at an angle that is inversely proportional to their size. Large particles generate a diffraction pattern at low scattering angles with high intensity, whereas small particles give rise to wide angle low intensity signals. Particle size distributions can be calculated if the intensity of light scattered from a sample are measured as a function of angle. The angular information is compared with a scattering model (e.g., Mie theory) in order to calculate the size distribution.

Generally, particle size is determined at room temperature and involves multiple analyses of the sample in question (e.g., at least 3 repeat measurements on the same sample) to yield an average value for the particle diameter.

For photon correlation spectroscopy, Z average (also called the cumulant mean or hydrodynamic diameter) is typically calculated from cumulants (monomodal) analysis.

For static light scattering measurements (and also for photon correlation spectroscopy), volume-based size parameters can be measured. For instance, the D(v,0.5) (where v means volume) is a size parameter whose value is defined as the point where 50% of the particles (volume basis) in the composition, as measured, have a size that is less than the D(v,0.5) value, and 50% of the particles in the composition have a size that is greater than the D(v,0.5) value. Similarly, the D(v,0.9) is a size parameter whose value is defined as the point where 90% (volume basis) of the particles in the composition have a size that is less than the D(v,0.9) value, and 10% of the particles in the composition have a size that is greater than the D(v,0.9) value.

Polymer microparticles for use herein are typically formed from materials that are sterilizable, substantially non-toxic and biodegradable. Such materials include poly(α-hydroxy acids), polyhydroxybutyric acids, polylactones (e.g., polycaprolactones), polyorthoesters, polyanhydrides, tyrosine-derived polycarbonates or polyester-amides, and polycyanoacrylates (e.g., polyalkylcyanoacrylate or "PACA"). More typically, microparticles for use with the present invention are polymer microparticles derived from poly(α-hydroxy acids), for example, from a poly(lactide) ("PLA") such as poly(D,L-lactide), a copolymer of lactide and glycolide, such as a poly(D,L-lactide-co-glycolide) ("PLG"), or a copolymer of D,L-lactide and caprolactone. The polymer microparticles may be derived from any of various polymeric starting materials which have a variety of molecular weights and, in the case of the copolymers, such as PLG, a variety of monomer (e.g., lactide:glycolide) ratios, the selection of which will be largely a matter of choice, depending in part on the coadministered species. These parameters are discussed further below.

"Zeta potential," as used herein, refers to the electrical potential that exists across the interface of all solids and liquids, e.g., the potential across the diffuse layer of ions surrounding a charged colloidal particle. Zeta potential can be calculated from electrophoretic mobilities, i.e., the rates at which colloidal particles travel between charged electrodes placed in contact with the substance to be measured, using techniques well known in the art.

The term "surfactant" as used herein includes dispersing agents, suspending agents, emulsion stabilizers and detergents. Cationic surfactants for use in the polymer microparticle compositions of the present invention include, for example, cetyltrimethylammonium bromide or "CTAB" (e.g., cetrimide), benzalkonium chloride, DDA (dimethyl dioctodecyl ammonium bromide), DOTAP (dioleoyl-3-trimethylammonium-propane), and the like. Anionic surfactants include, for example, SDS (sodium dodecyl sulfate), SLS (sodium lauryl sulfate), DSS (disulfosuccinate), sulphated fatty alcohols, and the like. Nonionic surfactants include, for example, PVA (polyvinylalcohol), povidone (also known as polyvinylpyrrolidone or PVP), sorbitan esters, polysorbates, polyoxyethylated glycol monoethers, polyoxyethylated alkyl phenols, poloxamers, and the like.

A "monosaccharide" is a polyhydric alcohol, i.e., an alcohol that further comprises either an aldehyde group (in which case the monosaccharide is an aldose) or a keto group (in which case the monosaccharide is a ketose). Monosaccharides typically contain from 3-10 carbons. Moreover, monosaccharides commonly have the empirical formula $(CH_2O)_n$ where n is an integer of three or greater, typically 3-10. Examples of 3-6 carbon aldoses include glyceraldehyde, erythrose, threose, ribose, 2-deoxyribose, arabinose, xylose, lyxose, allose, altrose, glucose, mannose, gulose, idose, galactose, and talose. Examples of 3-6 carbon ketoses include dihydroxyacetone, erythrulose, ribulose, xylulose, psicose, fructose, sorbose, and tagatose. Naturally occurring monosaccharides are normally found in the D-isomer form, as opposed to the L-form. An "oligosaccharide" refers to a relatively short monosaccharide polymer, i.e., one containing from 2 to 30 monosaccharide units. A "polysaccharide" is a monosaccharide polymer that is beyond oligosaccharide length (i.e., one containing more than 30 monosaccharide units). Moreover, as used herein, the term "polysaccharide"

also refers to a monosaccharide polymer that contain two or more linked monosaccharides. To avoid any ambiguity, the second definition is to be applied at all times, unless there are explicit indications to the contrary. The term "polysaccharide" also includes polysaccharide derivatives, such as amino-functionalized and carboxyl-functionalized polysaccharide derivatives, among many others. Monosaccharides are typically linked by glycosidic linkages.

As used herein the term "saccharide" encompasses monosaccharides, oligosaccharides and polysaccharides. A "saccharide-containing species" is a molecule, at least a portion of which is a saccharide. Examples include saccharide antigens, antigens comprising saccharides conjugated to carrier peptides, and so forth.

A "polynucleotide" is a nucleic acid polymer. As used herein, a "polynucleotide" can include as few as 5, 6, 7 or 8 nucleotides. Furthermore, a "polynucleotide" can include both double- and single-stranded sequences and refers to, but is not limited to, cDNA from viral, procaryotic or eucaryotic mRNA, genomic RNA and DNA sequences from viral (e.g. RNA and DNA viruses and retroviruses) or procaryotic DNA, and synthetic DNA sequences. The term also captures sequences that include any of the known base analogs of DNA and RNA. The term further includes modifications, such as deletions, additions and substitutions (generally conservative in nature), to a native sequence, for example, where the nucleic acid molecule encodes an antigenic protein. These modifications may be deliberate, as through site-directed mutagenesis, or may be accidental, such as through mutations of hosts that produce antigens.

As define herein an "oligonucleotide" is a polynucleotide having in the range of 5 to 100 nucleotides and more preferably 5 to 30 nucleotides in size.

As used herein, the phrase "nucleic acid" refers to DNA, RNA, or chimeras formed therefrom.

A "polynucleotide-containing species" is a molecule, at least a portion of which is a polynucleotide. Examples include RNA vector constructs, DNA vector constructs and so forth.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, for example, such that the protein maintains the ability to elicit an immunological response or have a therapeutic effect on a subject to which the protein is administered.

A "polypeptide-containing species" is a molecule, at least a portion of which is a polypeptide. Examples include polypeptides, proteins including glycoproteins, saccharide antigens conjugated to carrier proteins, and so forth.

The term "pharmaceutical" refers to biologically active compounds such as antibiotics, antiviral agents, growth factors, hormones, antigens and the like.

The term "adjuvant" refers to any substance that assists or modifies the action of a pharmaceutical, including but not limited to immunological adjuvants, which increase or diversify the immune response to an antigen. Hence, immunological adjuvants are compounds that are capable of potentiating an immune response to antigens. Immunological adjuvants can potentiate humoral and/or cellular immunity.

By "antigen" is meant a molecule that contains one or more epitopes capable of stimulating a host's immune system to make a cellular antigen-specific immune response when the antigen is presented, or a humoral antibody response. An antigen may be capable of eliciting a cellular and/or humoral response by itself or when present in combination with another molecule.

An "epitope" is that portion of an antigenic molecule or antigenic complex that determines its immunological specificity. An epitope is within the scope of the present definition of antigen. Commonly, an epitope is a polypeptide or polysaccharide in a naturally occurring antigen. In artificial antigens it can be a low molecular weight substance such as an arsanilic acid derivative. An epitope will react specifically in vivo or in vitro with, for example, homologous antibodies or T lymphocytes. Alternative descriptors are antigenic determinant, antigenic structural grouping and haptenic grouping.

Frequently, an epitope will include between about 5-15 amino acids. Epitopes of a given protein can be identified using any number of epitope mapping techniques, well known in the art. See, e.g., *Epitope Mapping Protocols in Methods in Molecular Biology*, Vol. 66 (Glenn E. Morris, Ed., 1996) Humana Press, Totowa, N.J. For example, linear epitopes may be determined by, for example, concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715. Similarly, conformational epitopes are readily identified by determining spatial conformation of amino acids such as by, e.g., x-ray crystallography and two-dimensional nuclear magnetic resonance. See, e.g., *Epitope Mapping Protocols*, supra.

The term "antigen" as used herein denotes both subunit antigens, i.e., antigens which are separate and discrete from a whole organism with which the antigen is associated in nature, as well as killed, attenuated or inactivated bacteria, viruses, parasites or other pathogens or tumor cells. Antibodies such as anti-idiotype antibodies, or fragments thereof, and synthetic peptide mimotopes, which can mimic an antigen or antigenic determinant, are also captured under the definition of antigen as used herein.

Similarly, an oligonucleotide or polynucleotide that expresses an immunogenic protein, or antigenic determinant in vivo, such as in nucleic acid immunization applications, is also included in the definition of antigen herein.

Furthermore, for purposes of the present invention, an "antigen" refers to a protein having modifications, such as deletions, additions and substitutions (generally conservative in nature), to the native sequence, as long as the protein maintains the ability to elicit an immunological response. These modifications may be deliberate, as through site-directed mutagenesis, or may be accidental, such as through mutations of hosts which produce the antigens.

An "immunological response" or "immune response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition such as an immunogenic composition or a vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) *J. Immunol.* 151:4189-4199; Doe et al. (1994) *Eur. J. Immunol.* 24:2369-2376; and the examples below.

Hence, an immunological response may include, for example, one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art, for instance, radioimmunoassays and ELISAs.

The immunogenic compositions of the present invention display "enhanced immunogenicity" when they possess a greater capacity to elicit an immune response than the immune response elicited by an equivalent amount of the antigen in a differing composition. Thus, a composition may display "enhanced immunogenicity," for example, because the composition generates a stronger immune response, or because a lower dose of antigen is necessary to achieve an immune response in the subject to which it is administered. Such enhanced immunogenicity can be determined, for example, by administering the compositions of the invention, and antigen controls, to animals and comparing assay results of the two.

As used herein, "treatment" (including variations thereof, for example, "treat" or "treated") refers to any of (i) the prevention of a pathogen or disorder in question (e.g. cancer or a pathogenic infection, as in a traditional vaccine), (ii) the reduction or elimination of symptoms, and (iii) the substantial or complete elimination of the pathogen or disorder in question. Treatment may be effected prophylactically (prior to arrival of the pathogen or disorder in question) or therapeutically (following arrival of the same).

The terms "effective amount" or "pharmaceutically effective amount" of an immunogenic composition of the present invention refer herein to a sufficient amount of the immunogenic composition to treat or diagnose a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

By "vertebrate subject" or "vertebrate animal" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are covered.

By "pharmaceutically acceptable" or "pharmacologically acceptable" is meant a material which is not biologically or otherwise undesirable, i.e., the material may be administered to an individual without causing any excessively undesirable biological effects in the individual or interacting in an excessively deleterious manner with any of the components of the composition in which it is contained.

The term "excipient" refers to any essentially accessory substance that may be present in the finished dosage form. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

By "physiological pH" or a "pH in the physiological range" is meant a pH in the range of approximately 7.2 to 8.0 inclusive, more typically in the range of approximately 7.2 to 7.6 inclusive.

As used herein, the phrase "vector construct" generally refers to any assembly that is capable of directing the expression of a nucleic acid sequence(s) or gene(s) of interest. A vector construct typically includes transcriptional promoter/enhancer or locus defining element(s), or other elements which control gene expression by other means such as alternate splicing, nuclear RNA export, post-translational modification of messenger, or post-transcriptional modification of protein. In addition, the vector construct typically includes a sequence which, when transcribed, is operably linked to the sequence(s) or gene(s) of interest and acts as a translation initiation sequence. The vector construct may also optionally include a signal that directs polyadenylation, a selectable marker, as well as one or more restriction sites and a translation termination sequence. In addition, if the vector construct is placed into a retrovirus, the vector construct may include a packaging signal, long terminal repeats (LTRs), and positive and negative strand primer binding sites appropriate to the retrovirus used (if these are not already present).

A "DNA vector construct" refers to a DNA molecule that is capable of directing the expression of a nucleic acid sequence(s) or gene(s) of interest.

One specific type of DNA vector construct is a plasmid, which is a circular episomal DNA molecule capable of autonomous replication within a host cell. Typically, a plasmid is a circular double stranded DNA, loop into which additional DNA segments can be ligated. pCMV is one specific plasmid that is well known in the art. A preferred pCMV vector is one which contains the immediate-early enhancer/promoter of CMV and a bovine growth hormone terminator.

It is described in detail in Chapman, B. S., et al. (1991) Nucleic Acids Res. 19:3979-3986.

Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. The RNA vector construct preferably comprises an RNA genome from a picornavirus, togavirus, flavivirus, coronavirus, paramyxovirus, yellow fever virus, or alphavirus (e.g., Sindbis virus, Semliki Forest virus, Venezuelan equine encephalitis virus, or Ross River virus), which has been modified by the replacement of one or more structural protein genes with a selected heterologous nucleic acid sequence encoding a product of interest. The RNA vector constructs can be obtained by transcription in vitro from a DNA template. Specific examples include Sindbis-virus-based plasmids (pSIN) such as pSINCP, described, for example, in U.S. Pat. Nos. 5,814,482 and 6,015,686, as well as in International Patent Applications WO 97/38087, WO 99/18226 and commonly owned WO 02/26209. The construction of such vectors, in general, is described in U.S. Pat. Nos. 5,814,482 and 6,015,686.

Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

B. GENERAL METHODS

1. Antigens

In some embodiments, compositions of the invention include one or more antigens, each antigen in an effective amount (e.g., an amount effective for use in therapeutic, prophylactic, or diagnostic methods in accordance with the invention). For example, the compositions of the present invention may be used to treat or prevent infections caused by any of the below-listed pathogens.

Antigens for use with the invention include, but are not limited to, one or more of the following antigens set forth below, or antigens derived from one or more of the pathogens set forth below:

A. Bacterial Antigens

Bacterial antigens suitable for use in the invention include proteins, polysaccharides, lipopolysaccharides, and outer membrane vesicles which may be isolated, purified or derived from a bacterium. In addition, bacterial antigens include bacterial lysates and inactivated bacteria formulations. Bacteria antigens can be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

Neisseria meningitides:

A meningococcal protein. Genome sequences for meningococcal serogroups A (Parkhill et al. (2000) Nature 404:502-506) and B (Tellelin et al. (2000) Science 287:1809-1815; WO00/66791) have been reported, and suitable antigens can be selected from the encoded polypeptides (e.g., Pizza et al. (2000) Science 287:1816-1820; WO99/24578; WO99/36544; WO99/57280; WO00/22430; and WO00/66741). Particular antigens include one or more one or more of the following five antigens (WO2004/032958): (1) a 'NadA' protein, preferably in oligomeric form (e.g. in trimeric form); (2) a '741' protein; (3) a '936' protein; (4) a '953' protein; and (5) a '287' protein. Other antigens for inclusion include Hsf adhesin and/or a transferrin-binding protein such as TbpB (WO2004/014419) and/or NspA.

An outer membrane vesicle (OMV) preparation from meningococcus. The term "OMV" includes any proteoliposomic vesicle obtained by disrupting a bacterial outer membrane to form vesicles of the outer membrane that include protein components of the outer membrane. OMVs are prepared artificially from bacteria (e.g. by detergent treatment, or by non-detergent means). The term also encompasses blebs, microvesicles (MVs (WO02/09643)) and 'native OMVs' ('NOMVs' (Katial et al. (2002) Infect. Immun. 70:702-707), which are naturally-occurring membrane vesicles that form spontaneously during bacterial growth and are released into culture medium. MVs can be obtained by culturing Neisseria in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture (e.g. refs. U.S. Pat. No. 6,180,111 and WO01/34642) describe Neisseria with high MV production. OMVs can be prepared in various ways. Methods for obtaining suitable preparations are disclosed in, for instance, the references cited herein. Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate (European Patent EP0011243B; and Fredriksen et al. (1991) NIPH Ann. 14 (2):67-80) being preferred for treating Neisseria) at a pH sufficiently high not to precipitate the detergent. The strain used for OMV preparation may have been modified e.g. to have a modified fur gene (WO98/56901), with nspA expression up-regulated and concomitant porA and cps knockout (WO02/09746), or as described in references WO01/09350; WO02/062378; WO2004/014417; WO2004/019977; and WO2004/048404. OMVs may be supplemented with additional proteins e.g. see references WO00/25811 and WO01/52885. The OMVs are preferably obtained from one of the following meningococcal serosubtypes: P1.7b, 4; P1.7, 16; P1.19, 15.

Streptococcus pneumoniae: Genome sequences for several strains of pneumococcus are available (Tettelin et al. (2001) Science 293:498-506; and Hoskins et al (2001) J Bacteriol 183:5709-5717) and can be subjected to reverse vaccinology (Rappuoli (2000) Curr Opin Microbiol 3:445-450; Rappuoli (2001) Vaccine 19:2688-2691; Masignani et al. (2002) Expert Opin Biol Ther 2:895-905; and Mora et al. (2003) Drug Discov Today 8:459-464) to identify suitable polypeptide antigens (Wizemann et al. (2001) Infect Immun 69:1593-1598; and Rigden et al. (2003) Crit. Rev Biochem Mol Biol 38:143-168). For example, the composition may include one or more of the following antigens: PhtA, PhtD, PhtB, PhtE, SpsA, LytB, LytC, LytA, Sp125, Sp101, Sp128, Sp130 and Sp130, as defined in reference WO02/22167. The composition may include more than one (e.g. 2, 3, 4, 5, 6, 7, 8, 9 10, 11, 12, 13 or 14) of these antigens.

*Streptococcus pyogenes* (Group A *Streptococcus*): Group A *Streptococcus* antigens include, for example, those disclosed in WO 02/34771; WO 2005/032582; WO 02/094851; Dale (1999) *Vaccine* 17:193-200; Dale (1996) *Vaccine* 14 (10): 944-948); and Ferretti et al. (2001) *PNAS USA* 98: 4658-4663.

*Moraxella catarrhalis*: *Moraxella* antigens include antigens identified in WO 02/18595; and WO 99/58562, outer membrane protein antigens (HMW-OMP), C-antigen, and/or LPS.

*Bordetella pertussis*: Pertussis antigens include *pertussis* holotoxin (PT) and filamentous haemagglutinin (FHA) from *B. pertussis*, optionally also combination with pertactin and/or agglutinogens 2 and 3 antigen.

Cellular *Bordetella pertussis* antigen, typically in the form of inactivated *B. pertussis* cells. Preparation of cellular *pertussis* antigens is well documented (e.g. see chapter 21 of *Vaccines*. (eds. Plotkin & Orenstein). 4th edition, 2004, ISBN: 0-7216-9688-0). Quantities of wP antigens can be expressed in international units (IU). For example, the NIBSC supplies the 'Third International Standard For Pertussis Vaccine' [NIBSC code: 66/303], which contains 46 IU per ampoule. Each ampoule contains the freeze-dried residue of 2.0 ml aliquots of an aqueous solution which contained 10 liters of bacterial suspension (equivalent to 180 opacity units in terms of the U.S. Opacity Standard) diluted with eight litres of M/15 Sorensen's buffer pH 7.0. As an alternative to the IU system, the 'OU' unit ("opacity units") is also used (e.g. 4 OU may be about 1 IU). There will typically be at least 8 IU/ml.

Acellular *Bordetella pertussis* antigen, including one or more of *pertussis* toxin (PT), filamentous haemagglutinin (FHA), pertactin (also known as the '69 kiloDalton outer membrane protein'), and fimbriae (e.g. agglutinogens 2 and 3). The invention preferably uses at least two of, and preferably all three of, PT, FHA and pertactin (i.e. without using fimbriae). FHA and pertactin may be treated with formaldehyde prior to use according to the invention. PT is preferably detoxified by treatment with formaldehyde and/or glutaraldehyde. As an alternative to this chemical detoxification procedure the PT may be a mutant PT in which enzymatic activity has been reduced by mutagenesis (Rappuoli et al. (1991) *TIBTECH* 9:232-238), but detoxification by chemical treatment is preferred. Quantities of acellular *pertussis* antigens are typically expressed in micrograms. There will typically be between 25-75 µg PT, about 25-75 µg FHA and about 10-20 µg pertactin per dose.

*Staphylococcus aureus*: Staph aureus antigens include *S. aureus* type 5 and 8 capsular polysaccharides optionally conjugated to nontoxic recombinant *Pseudomonas aeruginosa* exotoxin A, such as Staph VAX™, and antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and membrane-damaging toxins (optionally detoxified) that lyse eukaryotic cell membranes (hemolysins, leukotoxin, leukocidin). *Staph aureus* antigens includes, for example, antigens disclosed in Kuroda et al. (2001) *Lancet* 357 (9264):1225-1240; see also pages 1218-1219.

*Staphylococcus epidermidis*: *S. epidermidis* antigens include slime-associated antigen (SAA).

*Clostridium tetani* (Tetanus): Tetanus antigens include tetanus toxoid (TT), preferably used as a carrier protein in conjunction/conjugated with the compositions of the present invention.

Tetanus toxoid ('Tt'), disclosed in more detail in chapter 27 of *Vaccines*. (eds. Plotkin & Orenstein). 4th edition, 2004, ISBN: 0-7216-9688-0. Preferred tetanus toxoids are those prepared by formaldehyde treatment. Quantities of tetanus toxoid can be expressed in international units (IU). For example, the NIBSC supplies the 'Tetanus Toxoid Adsorbed Third International Standard 2000' (Sesardic et al. (2002) *Biologicals* 30:49-68; and NIBSC code: 98/552), which contains 469 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture [Module 1 of WHO's *The immunological basis for immunization series* (Galazka)]. For example, the NIBSC supplies 'The 1st International Reference Reagent for Tetanus Toxoid For Flocculation Test' [NIBSC code: TEFT] which contains 1000 Lf per ampoule. The concentration of tetanus toxoid in a composition of the invention is typically at least 100 IU/ml.

*Corynebacterium diphtheriae* (Diphtheria): Diphtheria antigens include diphtheria toxin, preferably detoxified, such as $CRM_{197}$. Additionally, antigens capable of modulating, inhibiting or associated with ADP ribosylation are contemplated for combination/co-administration/conjugation with the compositions of the present invention. The diphtheria toxoids may be used as carrier proteins.

Diphtheria toxoid ('Dt'), disclosed in more detail in chapter 13 of *Vaccines*. (eds. Plotkin & Orenstein). 4th edition, 2004, ISBN: 0-7216-9688-0. Preferred diphtheria toxoids are those prepared by formaldehyde treatment. Quantities of diphtheria toxoid can be expressed in international units (IU). For example, the NIBSC supplies the 'Diphtheria Toxoid Adsorbed Third International Standard 1999' (Sesardic et al. (2001) *Biologicals* 29:107-22; and NIBSC code: 98/560), which contains 160 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture (Module 1 of WHO's *The immunological basis for immunization series* (Galazka)). For example, the NIBSC supplies 'Diphtheria Toxoid, Plain' [NIBSC code: 69/017], which contains 300 LF per ampoule, and also supplies 'The 1st International Reference Reagent For Diphtheria Toxoid For Flocculation Test' [NIBSC code: DIFT] which contains 900 Lf per ampoule. The concentration of diphtheria toxoid in a composition of invention is typically at least 50 IU/ml.

*Haemophilus influenzae* B (Hib): Hib antigens include a Hib saccharide antigen.

*Pseudomonas aeruginosa*: *Pseudomonas* antigens include endotoxin A, Wzz protein, *P. aeruginosa* LPS, more particularly LPS isolated from PAO1 (O5 serotype), and Outer Membrane Proteins, including Outer Membrane Proteins F (OprF) (Price et al. (2001) *Infect Immun.* 69 (5):3510-3515).

*Legionella pneumophila*. Bacterial antigens can be derived from *Legionella pneumophila*.

*Streptococcus agalactiae* (Group B *Streptococcus*): Group B *Streptococcus* antigens include protein and saccharide antigens, such as those identified in WO 02/34771; WO 03/093306; WO 04/041157; WO 2005/002619; and Schuchat (1999) *Lancet* 353 (9146):51-66 (including proteins GBS 59, GBS 67, GBS 80, GBS 104, GBS 276 and GBS 322, and including saccharide antigens derived from serotypes Ia, Ib, Ia/c, II, III, IV, V, VI, VII and VIII).

*Neisserria gonorrhoeae*: Gonorrhoeae antigens include Por (or porin) protein, such as PorB (see, e.g., Zhu et al. (2004) *Vaccine* 22:660-669), a transferring binding protein, such as TbpA and TbpB (see, e.g., Price et al. (2004) *Infect. Immun.* 71 (1):277-283), an opacity protein (such as Opa), a reduction-modifiable protein (Rmp), and outer membrane vesicle (OMV) preparations (see, e.g., Plante et al. (2000) *J. Infect. Dis.* 182:848-855); WO 99/24578; WO 99/36544; WO 99/57280; and WO 02/079243).

*Chlamydia trachomatis. Chlamydia trachomatis* antigens include antigens derived from serotypes A, B, Ba and C (agents of trachoma, a cause of blindness), serotypes $L_1$, $L_2$ & $L_3$ (associated with Lymphogranuloma venereum), and serotypes, D-K. *Chlamydia* trachomas antigens also include antigens identified in WO 00/37494; WO 03/049762; WO 03/068811; and WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), MurG (CT761), CT396 and CT761, and specific combinations of these antigens.

*Treponema pallidum* (Syphilis): Syphilis antigens include TmpA antigen.

*Haemophilus ducreyi* (causing chancroid): *Ducreyi* antigens include outer membrane protein (DsrA).

*Enterococcus faecalis* or *Enterococcus faecium*: Antigens include a trisaccharide repeat and other *Enterococcus* derived antigens provided in U.S. Pat. No. 6,756,361.

*Helicobacter pylori*. *H pylori* antigens include Cag, Vac, Nap, HopX, HopY and urease antigen.

*Staphylococcus saprophyticus*. Antigens include the 160 kDa hemagglutinin of *S. saprophyticus* antigen.

*Yersinia enterocolitica* Antigens include LPS (Xu et al. (2002) *Infect. Immun.* 70 (8): 4414-4423).

*E. coli*: *E. coli* antigens can be derived from enterotoxigenic *E. coli* (ETEC), enteroaggregative *E. coli* (EAggEC), diffusely adhering *E. coli* (DAEC), enteropathogenic *E. coli* (EPEC), or enterohemorrhagic *E. coli* (EHEC).

*Bacillus anthracis* (anthrax). *B. anthracis* antigens are optionally detoxified and can be selected from A-components (lethal factor (LF) and edema factor (EF)), both of which can share a common B-component known as protective antigen (PA). In certain embodiments, the compositions of the present invention do not include an anthrax antigen.

*Yersinia pestis* (plague): Plague antigens include F1 capsular antigen (Gosfeld et al. (2003) *Infect. Immun.* 71 (1): 374-383), LPS (Fields et al. (1999) *Infect. Immun.* 67 (10): 5395-5408), *Yersinia pestis* V antigen (Hill et al. (1997) *Infect. Immun.* 65 (11): 4476-4482).

*Mycobacterium tuberculosis*: Tuberculosis antigens include lipoproteins, LPS, BCG antigens, a fusion protein of antigen 85B (Ag85B) and ESAT-6 optionally formulated in cationic lipid vesicles (Olsen et al. (2004) *Infect. Immun.* 72 (10): 6148-6150), *Mycobacterium tuberculosis* (Mtb) isocitrate dehydrogenase associated antigens (Banerjee et al. (2004) *Proc. Natl. Acad. Sci. USA* 101 (34):12652-12657), and MPT51 antigens (Suzuki et al. (2004) *Infect. Immun.* 72 (7):3829-3837).

*Rickettsia*: Antigens include outer membrane proteins, including the outer membrane protein A and/or B (OmpB) (Chao et al. (2004) *Biochim. Biophys. Acta.* 1702 (2):145-152), LPS, and surface protein antigen (SPA) (Carl et al. (1989) *J. Autoimmun.* 2 Suppl:81-91).

*Listeria monocytogenes*. Bacterial antigens can be derived from *Listeria monocytogenes*.

*Chlamydia pneumoniae*: Antigens include those identified in WO 02/02606.

*Vibrio cholerae*: Antigens include proteinase antigens, LPS, particularly lipopolysaccharides of *Vibrio cholerae* II, O1 Inaba O-specific polysaccharides, *V. cholera* O139, antigens of IEM108 vaccine (Liang et al. (2003) *Infect. Immun.* 71 (10):5498-5504), and Zonula occludens toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, Noppa et al. (2001) *Infect. Immun.* 69 (5):3323-3334), VlsE Antigenic Variation Protein (Lawrenz et al. (1999) *J. Clin. Microbiol.* 37 (12): 3997-4004).

*Porphyromonas gingivalis*: Antigens include *P. gingivalis* outer membrane protein (OMP).

*Klebsiella*: Antigens include OMPs, including OMP A, and polysaccharides optionally conjugated to tetanus toxoid.

Other bacterial antigens include capsular antigens, polysaccharide antigens or protein antigens of any of the above. Further bacterial antigens also include outer membrane vesicle (OMV) preparations. Additionally, antigens include live, attenuated, and/or purified versions of any of the aforementioned bacteria. Antigens can be derived from gram-negative or gram-positive bacteria. Antigens can be derived from aerobic or anaerobic bacteria.

Additionally, any of the above bacterial-derived saccharides (polysaccharides, LPS, LOS or oligosaccharides) can be conjugated to another agent or antigen, such as a carrier protein (for example $CRM_{197}$). Such conjugation can be direct conjugation effected by reductive amination of carbonyl moieties on the saccharide to amino groups on the protein, as provided in U.S. Pat. No. 5,360,897; and Roy et al. (1984) *Can. J. Biochem. Cell Biol.* 62 (5):270-275. In another embodiment, the saccharides can be conjugated through a linker, such as, with succinamide or other linkages provided in Hermanson, G. T., *Bioconjugate Techniques,* 1st ed., Academic Press (1996) and Wong, S. S., *CRC, Chemistry of protein Conjugation and Cross-Linking,* 1st ed., CRC-Press (1991). Suitable saccharide antigens include but are not limited to conjugated capsular saccharides from the following bacteria:

*Haemophilus influenzae* type B ('Hib'). Hib conjugates are disclosed in more detail in chapter 14 of *Vaccines*. (eds. Plotkin & Orenstein). 4th edition, 2004, ISBN: 0-7216-9688-0. The saccharide moiety of a Hib conjugate may comprise full-length polyribosylribitol phosphate (PRP) as prepared from Hib bacteria, or it may comprise fragments of full-length PRP. The amount of Hib conjugate, measured as saccharide, in compositions of the invention is typically between 10 and 30 µg/ml. Administration of the Hib conjugate preferably results in an anti-PRP antibody concentration of $\geq 0.15$ µg/ml, and more preferably $\geq 1$ µg/ml, and these are the standard acceptable response thresholds.

*Neisseria meningitidis* serogroup C ('MenC'). Conjugate vaccines against MenC have been approved for human use, and include MENJUGATE™ [Jones (2001) *Curr Opin Investig Drugs* 2:47-49], MENINGITEC™ and NEISVAC-C™. Serogroup C saccharides may be prepared from either OAc+ or OAc− strains.

*Neisseria meningitidis* serogroup A ('MenA'). Preferably at least 50% (e.g. at least 60%, 70%, 80%, 90%, 95% or more) of the mannosamine residues are O-acetylated at the C-3 position.

*Neisseria meningitidis* serogroup W135 ('MenW135').

*Neisseria meningitidis* serogroup Y ('MenY').

*Streptococcus pneumoniae* (e.g. Watson (2000) *Pediatr Infect Dis J* 19:331-332; Rubin (2000) *Pediatr Clin North Am*

47:269-285; and Jedrzejas (2001) *Microbiol Mol Biol Rev* 65:187-207). It is preferred to include saccharides from more than one serotype of *S. pneumoniae*: mixtures of polysaccharides from 23 different serotype are widely used, as are conjugate vaccines with polysaccharides from between 5 and 11 different serotypes (Zielen et al. (2000) *Infect. Immun.* 68:1435-1440). For example, PrevNar™ (Darkes & Plosker (2002) *Paediatr Drugs* 4:609-630) contains antigens from seven serotypes (4, 6B, 9V, 14, 18C, 19F, and 23F) with each saccharide individually conjugated to CRM197 by reductive amination, with 2 µg of each saccharide per 0.5 ml dose (4 µg of serotype 6B). Compositions of the invention preferably include at least serotypes 6B, 14, 19F and 23F. Further serotypes are preferably selected from: 1, 3, 4, 5, 7F, 9V and 18C. The amount of a pneumococcal conjugate, measured as saccharide, in compositions of the invention is typically between 2 and 20 µg/ml for each serotype.

*Streptococcus pyogenes* ('GAS') e.g. as described in Sabharwal et al. (2006) *J Infect Dis* 193:129-135.

*Streptococcus agalactiae* ('GBS') e.g. as described in Baker & Edwards (2003) *Arch Dis Child* 88:375-378; Paoletti & Kasper (2002) *J Infect Dis* 186:123-126; Palazzi et al. (2004) *J Infect Dis* 190:558-564; Heath & Feldman (2005) *Expert Rev Vaccines* 4:207-218; Paoletti & Kasper (2003) *Expert Opin Biol Ther* 3:975-984. Saccharides from GBS serotypes Ia, Ib and/or III will typically be included. GBS serotypes IV, V and VII may also be used.

B. Viral Antigens

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens can be derived from viruses propagated on cell culture or other substrate or expressed recombinantly. Viral antigens preferably include epitopes which are exposed on the surface of the virus during at least one stage of its life cycle. Viral antigens are preferably conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans). Influenza antigens may be derived from viruses grown in eggs or cell culture.

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., Johnstone et al. (2004) *J. Gen. Virol.* 85 (Pt 11):3229-3238). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from a Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 and NSP-4. Togavirus antigens are preferably selected from E1, E2 and E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis B virus surface antigen ('HBsAg'). A typical HBsAg will be expressed by recombinant DNA methods in a yeast, such as a *Saccharomyces cerevisiae, Pichia pastoris* or *Hanensula polymorpha*. The HBsAg is preferably non-glycosylated. It may take the form of substantially-spherical particles including a lipid matrix comprising phospholipids and, optionally, phosphatidylinositol. The HBsAg is preferably from HBV subtype adw2. There will typically be between 1 and 50 μg HBsAg.

Hepatitis A virus: Hepatitis A virus antigen ('HAV'), as disclosed in chapter 15 of *Vaccines*. (eds. Plotkin & Orenstein). 4th edition, 2004, ISBN: 0-7216-9688-0. A preferred HAV component is based on inactivated virus, and inactivation can be achieved by formalin treatment. Virus can be grown on human embryonic lung diploid fibroblasts, such as MRC-5 cells. A preferred HAV strain is HM175, although CR326F can also be used. The cells can be grown under conditions that permit viral growth. The cells are lysed, and the resulting suspension can be purified by ultrafiltration and gel permeation chromatography. The amount of HAV antigen, measured in EU (Elisa Units), is typically at least 600 EU/ml.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions (Houghton et al. (1991) *Hepatology* 14:381-388).

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L) and nonstructural proteins (NS). Commercially available Rabies virus vaccine comprise killed virus grown on human diploid cells or fetal rhesus lung cells.

Caliciviridae: Viral antigens may be derived from Calciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, rex, rev, nef, vif, vpu, and vpr. HIV antigens may be selected from gag (p24gag and p55gag), env (gp160 and gp41), pol, tat, nef, rev vpu, miniproteins, (preferably p55 gag and gp140v delete). HIV antigens may be derived from one or more of the following strains: $HIV_{IIIb}$, $HIV_{SF2}$, $HIV_{LAV}$, $HIV_{LAI}$, $HIV_{MN}$, $HIV-1_{CM235}$, $HIV-1_{US4}$.

Reovirus: Viral antigens may be derived from a Reovirus, such as an Orthoreovirus, a Rotavirus, an Orbivirus, or a Coltivirus. Reovirus antigens may be selected from structural proteins λ1, λ2, λ3, μ1, μ2, σ1, σ2, or σ3, or nonstructural proteins σNS, μNS, or σ1s. Preferred Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Preferred Rotavirus antigens include VP4 (or the cleaved product VP5 and VP8), and VP7.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HDV). Viral antigens may be derived HDV, particularly δ-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomyavirus viruses include BK virus and JK virus. Polyomavirus antigens may be selected from VP1, VP2 or VP3.

Other antigens, compositions, methods, and microbes for use in the invention are described in Plotkin, S. A. et al., *Vaccines*, 4th ed., W.B. Saunders Co. (2004); Murray, P. R. et al., *Medical Microbiology* 5th ed., Mosby Elsevier (2005); Joklik, W. K. (ed.), *Virology*, 3rd ed., Appleton & Lange (1988); Howley, P. M. et al. (eds.), *Fundamental Virology*, 4th ed., Lippincott Williams & Wilkins (1991); and Fields, B. N. et al. (eds.), *Fields Virology*, 4th ed., Lippincott Williams & Wilkins (2001).

C. Fungal Antigens

Fungal antigens for use in the invention can be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum*

*nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T verrucosum* var. *album,* var. *discoides,* var. *ochraceum, Trichophyton violaceum,* and/or *Trichophyton faviforme.*

Fungal pathogens may be derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Saccharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing a fungal antigens are well known in the art (see U.S. Pat. No. 6,333,164). In a preferred method, a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

D. STD Antigens

The compositions of the invention can include one or more antigens derived from a sexually transmitted disease (STD). Such antigens can provide for prophylactis or therapy for STDs such as chlamydia, genital herpes, hepatits (such as HCV), genital warts, gonorrhoea, syphilis and/or chancroid (see WO 00/15255). Antigens may be derived from one or more viral or bacterial STDs. Viral STD antigens for use in the invention may be derived from, for example, HIV, herpes simplex virus (HSV-1 and HSV-2), human papillomavirus (HPV), and hepatitis (HCV). Bacterial STD antigens for use in the invention may be derived from, for example, *Neiserria gonorrhoeae, Chlamydia trachomatis, Treponema pallidum, Haemophilus ducreyi, E. coli,* and *Streptococcus agalactiae.* Examples of specific antigens derived from these pathogens are described above.

E. Respiratory Antigens

The compositions of the invention can include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacteria which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis,* and *Moraxella catarrhalis.* Examples of specific antigens derived from these pathogens are described above.

F. Pediatric Vaccine Antigens

The compositions of the invention may include one or more antigens suitable for use in pediatric subjects. Pediatric subjects are typically less than about 3 years old, or less than about 2 years old, or less than about 1 years old. Pediatric antigens can be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli.* Examples of specific antigens derived from these pathogens are described above.

G. Antigens Suitable for Use in Elderly or Immunocompromised Individuals

The compositions of the invention can include one or more antigens suitable for use in elderly or immunocompromised individuals. Elderly subjects are typically over the age of about 50, 55, 60, 65, 70 or 75 years. Such individuals may need to be vaccinated more frequently, with higher doses or with adjuvanted formulations to improve their immune response to the targeted antigens. Antigens which may be targeted for use in elderly or immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae,* Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

H. Antigens Suitable for Use in Adolescent Vaccines

The compositions of the invention can include one or more antigens suitable for use in adolescent subjects. Adolescent subjects are typically between about 10 and about 20 years old, or between about 12 to about 14 and about 19 or 20 years old. Adolescents may be in need of a boost of a previously administered pediatric antigen. Pediatric antigens which may be suitable for use in adolescents are described above. In addition, adolescents may be targeted to receive antigens derived from an STD pathogen in order to ensure protective or therapeutic immunity before the beginning of sexual activity. STD antigens which may be suitable for use in adolescents are described above.

I. Tumor Antigens

The compositions of the invention can include one or more tumor or cancer antigens. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen. A tumor antigen can further be, for example, a polynucleotide-containing tumor antigen that expresses a polypeptide-containing tumor antigen, for instance, an RNA vector construct or a DNA vector construct, such as plasmid DNA.

Tumor antigens include (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

Tumor antigens can be, for example, (a) full length molecules associated with cancer cells, (b) homologs and modified forms of the same, including molecules with deleted, added and/or substituted portions, and (c) fragments of the same. Tumor antigens can be provided in recombinant form. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Other tumor antigens include p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KPI, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like. These as well as other cellular components are described for example in United States Patent Publication No. 2002/0007173 and references cited therein.

Polynucleotide-containing antigens in accordance with the present invention typically comprise polynucleotides that encode polypeptide cancer antigens such as those listed above. Preferred polynucleotide-containing antigens include DNA or RNA vector constructs, such as plasmid vectors (e.g., pCMV), which are capable of expressing polypeptide cancer antigens in vivo.

Tumor antigens may be derived, for example, from mutated or altered cellular components. After alteration, the cellular components no longer perform their regulatory functions, and hence the cell may experience uncontrolled growth. Representative examples of altered cellular components include ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor. These as well as other cellular components are described for example in U.S. Pat. No. 5,693, 522 and references cited therein.

Bacterial and viral antigens, may be used in conjunction with the compositions of the present invention for the treatment of cancer. Carrier proteins, such as $CRM_{197}$, tetanus toxoid, or *Salmonella typhimurium* antigen may be used in conjunction/conjugation with compounds of the present invention for treatment of cancer. The cancer antigen combination therapies will show increased efficacy and bioavailability as compared with existing therapies.

Additional information on cancer or tumor antigens can be found, for example, in Moingeon (2001) *Vaccine* 19:1305-1326; Rosenberg (2001) *Nature* 411:380-384; Dermine et al.

(2002) *Brit. Med. Bull.* 62:149-162; Espinoza-Delgado (2002) *The Oncologist* 7 (suppl 3):20-33; Davis et al. (2003) *J. Leukocyte Biol.* 23:3-29; Van den Eynde et al. (1995) *Curr. Opin. Immunol.* 7:674-681; Rosenberg (1997) *Immunol. Today* 18:175-182; Offringa et al. (2000) *Curr. Opin. Immunol.* 2:576-582; Rosenberg (1999) *Immunity* 10:281-287; Sahin et al. (1997) *Curr. Opin. Immunol.* 9:709-716; Old et al. (1998) *J. Exp. Med.* 187:1163-1167; Chaux et al. (1999) *J. Exp. Med.* 189:767-778; Gold et al. (1965) *J. Exp. Med.* 122:467-468; Livingston et al. (1997) *Cancer Immunol. Immunother.* 45:1-6; Livingston et al. (1997) *Cancer Immunol. Immunother.* 45:10-19; Taylor-Papadimitriou (1997) *Immunol. Today* 18:105-107; Zhao et al. (1995) *J. Exp. Med.* 182:67-74; Theobald et al. (1995) *Proc. Natl. Acad. Sci. USA* 92:11993-11997; Gaudernack (1996) *Immunotechnology* 2:3-9; WO 91/02062; U.S. Pat. No. 6,015,567; WO 01/08636; WO 96/30514; U.S. Pat. No. 5,846,538; and U.S. Pat. No. 5,869,445.

Further antigens may also include an outer membrane vesicle (OMV) preparation.

Additional formulation methods and antigens (especially tumor antigens) are provided in U.S. Patent Publication No. 2004/0202680. See also U.S. Pat. No. 6,884,435.

2. Immunological Adjuvants

In certain embodiments, the vaccines of the invention are administered in conjunction with other immunoregulatory agents. In particular, compositions will commonly include an adjuvant. For example, adjuvants may be administered concurrently with antigen-containing compositions, e.g., in the same composition or in separate compositions. Alternatively, adjuvants may be administered prior or subsequent to antigen administration.

Adjuvants for use with the invention include, but are not limited to, one or more of the following set forth below:

A. Mineral Containing Compositions

Mineral containing compositions suitable for use as adjuvants include mineral salts, such as aluminum salts and calcium salts. The invention includes mineral salts such as hydroxides (e.g. oxyhydroxides), phosphates (e.g. hydroxyphosphates, orthophosphates), sulfates, etc. (see, e.g., *Vaccine Design. The Subunit and Adjuvant Approach* (Powell, M. F. and Newman, M. J. eds.) (New York: Plenum Press) 1995, Chapters 8 and 9), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO 00/23105).

Aluminum salts may be included in vaccines of the invention such that the dose of $Al^{3+}$ is between 0.2 and 1.0 mg per dose.

In one embodiment, the aluminum based adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. In another embodiment, the aluminum based adjuvant is aluminum phosphate adjuvant ($AlPO_4$) or aluminum hydroxyphosphate, which contains phosphate groups in place of some or all of the hydroxyl groups of aluminum hydroxide adjuvant. Preferred aluminum phosphate adjuvants provided herein are amorphous and soluble in acidic, basic and neutral media.

In another embodiment, the adjuvant comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. In another embodiment, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

B. Oil-Emulsions

Oil-emulsion compositions and formulations suitable for use as adjuvants (with or without other specific immunostimulating agents such as muramyl peptides or bacterial cell wall components) include squalene-water emulsions, such as MF59 (5% Squalene, 0.5% Tween 80, and 0.5% Span 85, formulated into submicron particles using a microfluidizer). See WO 90/14837. See also, Podda (2001) *Vaccine* 19: 2673-2680; Frey et al. (2003) *Vaccine* 21:4234-4237. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyethylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE), for example, the submicron oil-in-water emulsion known as "MF59" (WO 90/14837; U.S. Pat. No. 6,299,884; U.S. Pat. No. 6,451,325; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) (New York: Plenum Press) 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in WO 90/14837; U.S. Pat. No. 6,299,884; and U.S. Pat. No. 6,451,325.

Complete Freund's adjuvant (CFA) and incomplete Freund's adjuvant (IFA) may also be used as adjuvants in the invention.

C. Saponin Formulations

Saponin formulations are also suitable for use as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin adjuvant formulations include STIMULON® adjuvant (Antigenics, Inc., Lexington, Mass.).

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO 96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of (an) additional detergent(s). See WO 00/07621.

A review of the development of saponin based adjuvants can be found in Barr et al. (1998) *Adv. Drug Del. Rev.* 32:247-271. See also Sjolander et al. (1998) *Adv. Drug Del. Rev.* 32:321-338.

D. Virosomes and Virus Like Particles (VLPs)

Virosomes and Virus Like Particles (VLPs) are also suitable as adjuvants. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO 03/024480; WO 03/024481; Niikura et al. (2002) *Virology* 293:273-280; Lenz et al. (2001) *J. Immunol.* 166 (9): 5346-5355; Pinto et al. (2003) *J. Infect. Dis.* 188:327-338; and Gerber et al. (2001) *J. Virol.* 75 (10):4752-4760. Virosomes are discussed further in, for example, Gluck et al. (2002) *Vaccine* 20:B10-B16. Immunopotentiating reconstituted influenza virosomes (IRIV) are used as the subunit antigen delivery system in the intranasal trivalent INFLEXAL™ product (Mischler and Metcalfe (2002) *Vaccine* 20 Suppl 5:B17-B23) and the INFLUVAC PLUS™ product.

E. Bacterial or Microbial Derivatives

Adjuvants suitable for use in the invention include bacterial or microbial derivatives such as:

(1) Non-toxic derivatives of enterobacterial lipopolysaccharide (LPS): Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives, e.g., RC-529. See Johnson et al. (1999) *Bioorg. Med. Chem. Lett.* 9:2273-2278.

(2) Lipid A Derivatives: Lipid A derivatives include derivatives of lipid A from *Escherichia coli* such as OM-174. OM-174 is described for example in Meraldi et al. (2003) *Vaccine* 21:2485-2491; and Pajak et al. (2003) *Vaccine* 21:836-842.

(3) Immunostimulatory oligonucleotides: Immunostimulatory oligonucleotides or polymeric molecules suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory. The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla et al. (2003) *Nucl. Acids Res.* 31 (9): 2393-2400; WO 02/26757; and WO 99/62923 for examples of possible analog substitutions. The adjuvant effect of CpG oligonucleotides is further discussed in Krieg (2003) *Nat. Med.* 9 (7):831-835; McCluskie et al. (2002) *FEMS Immunol. Med. Microbiol.* 32:179-185; WO 98/40100; U.S. Pat. No. 6,207,646; U.S. Pat. No. 6,239,116; and U.S. Pat. No. 6,429,199.

The CpG sequence may be directed to TLR9, such as the motif GTCGTT or TTCGTT. See Kandimalla et al. (2003) *Biochem. Soc. Trans.* 31 (part 3):654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al. (2003) *J. Immunol.* 170 (8):4061-4068; Krieg (2002) *TRENDS Immunol.* 23 (2): 64-65; and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) *BBRC* 306:948-953; Kandimalla et al. (2003) *Biochem. Soc. Trans.* 31 (part 3):664-658; Bhagat et al. (2003) *BBRC* 300:853-861; and WO03/035836.

Immunostimulatory oligonucleotides and polymeric molecules also include alternative polymer backbone structures such as, but not limited to, polyvinyl backbones (Pitha et al. (1970) *Biochem. Biophys. Acta* 204 (1):39-48; Pitha et al. (1970) *Biopolymers* 9 (8):965-977), and morpholino backbones (U.S. Pat. No. 5,142,047; U.S. Pat. No. 5,185,444). A variety of other charged and uncharged polynucleotide analogs are known in the art. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).

(4) ADP-ribosylating toxins and detoxified derivatives thereof: Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or *pertussis* ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al. (2002) *Infect. Immun.* 70 (6):3012-3019; Pizza et al. (2001) *Vaccine* 19:2534-2541; Pizza et al. (2000) *Int. J. Med. Microbiol.* 290 (4-5):455-461; Scharton-Kersten et al. (2000) *Infect. Immun.* 68 (9):5306-5313; Ryan et al. (1999) *Infect. Immun.* 67 (12):6270-6280; Partidos et al. (1999) *Immunol. Lett.* 67 (3):209-216; Peppoloni et al. (2003) *Vaccines* 2 (2): 285-293; and Pine et al. (2002) *J. Control Release* 85 (1-3): 263-270. Numerical reference for amino acid substitutions is preferably based on the alignments of the A and B subunits of ADP-ribosylating toxins set forth in Domenighini et al. (1995) *Mol. Microbiol.* 15 (6):1165-1167.

Compounds of formula I, II or III, or salts thereof, can also be used as adjuvants:

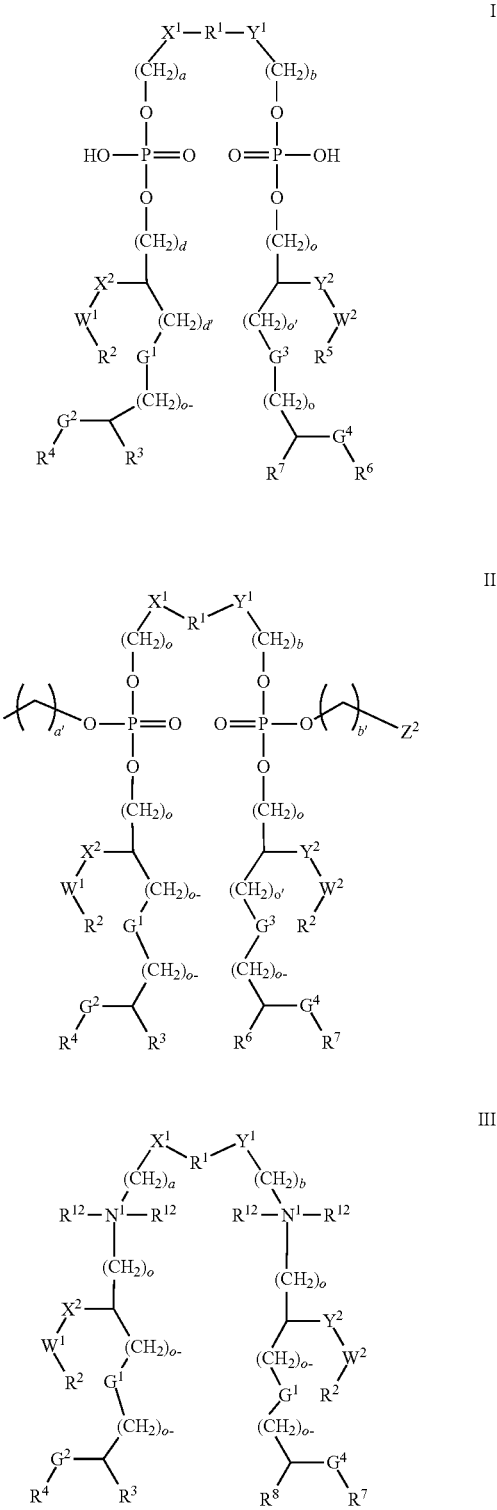

as defined in WO03/011223, such as 'ER 803058', 'ER 803732', 'ER 804053', ER 804058', 'ER 804059', 'ER 804442', 'ER 804680', 'ER 804764', ER 803022 or 'ER 804057' e.g.:

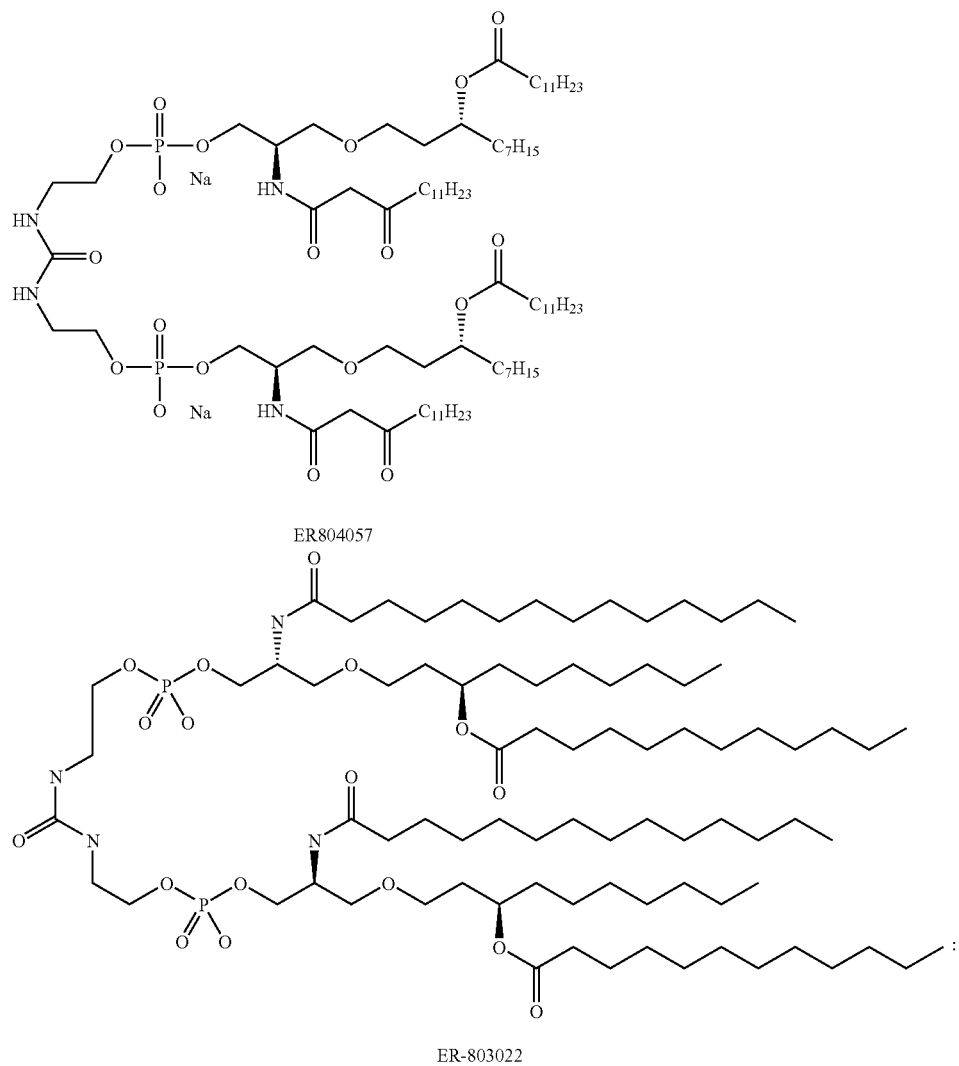

F. Human Immunomodulators

Human immunomodulators suitable for use as adjuvants include cytokines, such as interleukins (e.g. IL-1, IL-2, IL-4, IL-5, IL-6, IL-7, IL-12, etc.), interferons (e.g. interferon-γ), macrophage colony stimulating factor (M-CSF), and tumor necrosis factor (TNF).

G. Bioadhesives and Mucoadhesives

Bioadhesives and mucoadhesives may also be used as adjuvants. Suitable bioadhesives include esterified hyaluronic acid microspheres (Singh et al. (2001) *J. Cont. Release* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention (see WO 99/27960).

H. Liposomes

Examples of liposome formulations suitable for use as adjuvants are described in U.S. Pat. No. 6,090,406; U.S. Pat. No. 5,916,588; and EP Patent Publication No. EP 0 626 169.

I. Polyoxyethylene Ether and Polyoxyethylene Ester Formulations

Adjuvants suitable for use in the invention include polyoxyethylene ethers and polyoxyethylene esters (see, e.g., WO 99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations suitable for use as adjuvants are described, for example, in Andrianov et al. (1998) *Biomaterials* 19 (1-3):109-115; and Payne et al. (1998) *Adv. Drug Del. Rev.* 31 (3):185-196.

K. Muramyl Peptides

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds

Examples of imidazoquinoline compounds suitable for use as adjuvants include Imiquimod and its analogues, which are described further in Stanley (2002) *Clin. Exp. Dermatol.* 27 (7):571-577; Jones (2003) *Curr. Opin. Investig. Drugs* 4 (2): 214-218; and U.S. Pat. Nos. 4,689,338; 5,389,640; 5,268,376; 4,929,624; 5,266,575; 5,352,784; 5,494,916; 5,482,936; 5,346,905; 5,395,937; 5,238,944; and 5,525,612.

M. Thiosemicarbazone Compounds

Examples of thiosemicarbazone compounds suitable for use as adjuvants, as well as methods of formulating, manufacturing, and screening for such compounds, include those described in WO 04/60308. The thiosemicarbazones are particularly effective in the stimulation of human peripheral blood mononuclear cells for the production of cytokines, such as TNF-α.

N. Tryptanthrin Compounds

Examples of tryptanthrin compounds suitable for use as adjuvants, as well as methods of formulating, manufacturing, and screening for such compounds, include those described in WO 04/64759. The tryptanthrin compounds are particularly effective in the stimulation of human peripheral blood mononuclear cells for the production of cytokines, such as TNF-α.

O. Nucleoside Analogs

Various nucleoside analogs can be used as adjuvants, such as (a) Isatorabine (ANA-245; 7-thia-8-oxoguanosine):

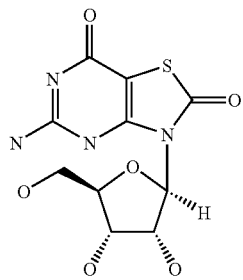 [SMILES: Nc1nc(=O)c2sc(=O)n([C@@H]3O[C@H](CO)[C@@H](O)[C@H]3O)c2[nH]1]

an U d prodrugs thereof; (b) ANA975; (c) ANA-025-1; (d) ANA380; (e) the compounds disclosed in U.S. Pat. No. 6,924,271; U.S. Publication No. 2005/0070556; and U.S. Pat. No. 5,658,731; (f) a compound having the formula:

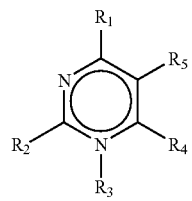

wherein:

$R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;

$R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

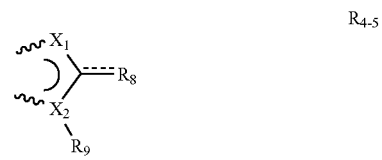

the binding being achieved at the bonds indicated by a ~~~

$X_1$ and $X_2$ are each independently N, C, O, or S;

$R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—($C_{1-6}$ alkyl), —$S(O)_pR_e$, or —C(O)—$R_d$;

$R_9$ is H, $C_{1-6}$ alkyl, substituted $C_{1-6}$ alkyl, heterocyclyl, substituted heterocyclyl or $R_{9a}$, wherein $R_{9a}$ is:

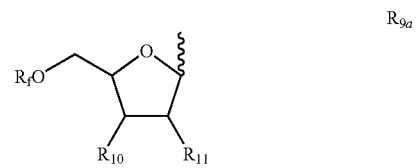

the binding being achieved at the bond indicated by a ~~~

$R_{10}$ and $R_{11}$ are each independently H, halo, $C_{1-6}$ alkoxy, substituted $C_{1-6}$ alkoxy, —$NR_aR_b$, or —OH;

each $R_a$ and $R_b$ is independently H, $C_{1-6}$ alkyl, substituted $C_{1-6}$ alkyl, —C(O)$R_d$, $C_{6-10}$ aryl;

each $R_c$ is independently H, phosphate, diphosphate, triphosphate, $C_{1-6}$ alkyl, or substituted $C_{1-6}$ alkyl;

each $R_d$ is independently H, halo, $C_{1-6}$ alkyl, substituted $C_{1-6}$ alkyl, $C_{1-6}$ alkoxy, substituted $C_{1-6}$ alkoxy, —$NH_2$, —$NH(C_{1-6}$ alkyl), —NH (substituted $C_{1-6}$ alkyl), —$N(C_{1-6}$ alkyl)$_2$, —N(substituted $C_{1-6}$ alkyl)$_2$, $C_{6-10}$ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, —C(O)$R_d$, phosphate, diphosphate, or triphosphate;

each n is independently 0, 1, 2, or 3;

each p is independently 0, 1, or 2; or or (g) a pharmaceutically acceptable salt of any of (a) to (f), a tautomer of any of (a) to (f), or a pharmaceutically acceptable salt of the tautomer.

P. Lipids Linked to a Phosphate-Containing Acyclic Backbone

Adjuvants containing lipids linked to a phosphate-containing acyclic backbone include the TLR4 antagonist E5564 (Wong et al. (2003) *J. Clin. Pharmacol.* 43 (7):735-742; US2005/0215517):

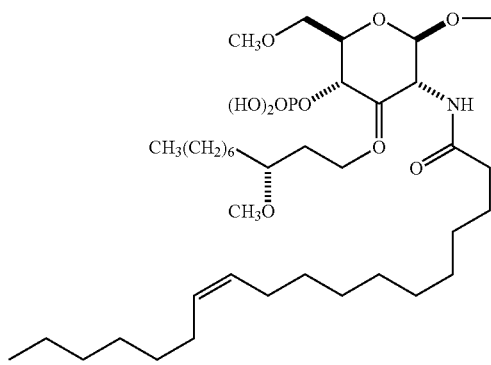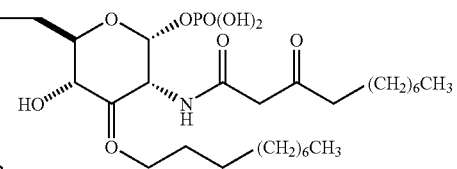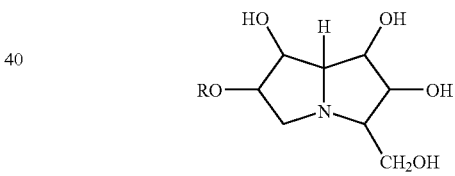

Q. Small Molecule Immunopotentiators (SMIPs)
SMIPs include:
N2-methyl-1-(2-methylpropyl)-1H-imidazo[4,5-c]quinoline-2,4-diamine;
N2,N2-dimethyl-1-(2-methylpropyl)-1H-imidazo[4,5-c]quinoline-2,4-diamine;
N2-ethyl-N2-methyl-1-(2-methylpropyl)-1H-imidazo[4,5-c]quinoline-2,4-diamine;
N2-methyl-1-(2-methylpropyl)-N2-propyl-1H-imidazo[4,5-c]quinoline-2,4-diamine;
1-(2-methylpropyl)-N2-propyl-1H-imidazo[4,5-c]quinoline-2,4-diamine;
N2-butyl-1-(2-methylpropyl)-1H-imidazo[4,5-c]quinoline-2,4-diamine;
N2-butyl-N2-methyl-1-(2-methylpropyl)-1H-imidazo[4,5-c]quinoline-2,4-diamine;
N2-methyl-1-(2-methylpropyl)-N2-pentyl-1H-imidazo[4,5-c]quinoline-2,4-diamine;
N2-methyl-1-(2-methylpropyl)-N2-prop-2-enyl-1H-imidazo[4,5-c]quinoline-2,4-diamine;
1-(2-methylpropyl)-2-[(phenylmethyl)thio]-1H-imidazo[4,5-c]quinolin-4-amine;
1-(2-methylpropyl)-2-(propylthio)-1H-imidazo[4,5-c]quinolin-4-amine;
2-[[4-amino-1-(2-methylpropyl)-1H-imidazo[4,5-c]quinolin-2-yl](methyl)amino]ethanol;
2-[[4-amino-1-(2-methylpropyl)-1H-imidazo[4,5-c]quinolin-2-yl](methyl)amino]ethyl acetate;
4-amino-1-(2-methylpropyl)-1,3-dihydro-2H-imidazo[4,5-c]quinolin-2-one;
N2-butyl-1-(2-methylpropyl)-N4,N4-bis(phenylmethyl)-1H-imidazo[4,5-c]quinoline-2,4-diamine;
N2-butyl-N2-methyl-1-(2-methylpropyl)-N4,N4-bis(phenylmethyl)-1H-imidazo[4,5-c]quinoline-2,4-diamine;
N2-methyl-1-(2-methylpropyl)-N4,N4-bis(phenylmethyl)-1H-imidazo[4,5-c]quinoline-2,4-diamine;
N2,N2-dimethyl-1-(2-methylpropyl)-N4,N4-bis(phenylmethyl)-1H-imidazo[4,5-c]quinoline-2,4-diamine;
1-{4-amino-2-[methyl(propyl)amino]-1H-imidazo[4,5-c]quinolin-1-yl}-2-methylpropan-2-ol;
1-[4-amino-2-(propylamino)-1H-imidazo[4,5-c]quinolin-1-yl]-2-methylpropan-2-ol;
N4,N4-dibenzyl-1-(2-methoxy-2-methylpropyl)-N2-propyl-1H-imidazo[4,5-c]quinoline-2,4-diamine.

R. Proteosomes

One adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of Neisseria meningitidis outer membrane and lipopolysaccharides. They have been used as adjuvants for influenza vaccines (WO02/072012).

S. Other Adjuvants

Other substances that act as immunostimulating agents are disclosed in Burdman, J. R. et al. (eds) (1995) (Vaccine Design: Subunit and Adjuvant Approach (Springer) (Chapter 7) and O'Hagan, D. T. (2000) (Vaccine Adjuvants: Preparation Methods and Research Protocols (Humana Press) (Volume 42 of Methods in Molecular Medicine series)).

Further useful adjuvant substances include:
Methyl inosine 5'-monophosphate ("MIMP") (Signorelli & Hadden (2003) Int. Immunopharmacol. 3 (8):1177-1186).
A polyhydroxylated pyrrolizidine compound (WO2004/064715), such as one having formula:

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepicasuarine, etc.

A gamma inulin (Cooper (1995) Pharm. Biotechnol. 6:559-580) or derivative thereof, such as algammulin.
Compounds disclosed in PCT/US2005/022769.
Compounds disclosed in WO2004/87153, including:
Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (U.S. Pat. No. 6,605,617; WO 02/18383), Hydrapthalamide compounds, Benzophenone compounds, Isoxazole compounds, Sterol compounds, Quinazilinone compounds, Pyrrole compounds (WO2004/018455), Anthraquinone compounds, Quinoxaline compounds, Triazine compounds, Pyrazalopyrimidine compounds, and Benzazole compounds (WO03/082272).

Loxoribine (7-allyl-8-oxoguanosine) (U.S. Pat. No. 5,011,828).

A formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE: DOPE"). Formulations containing (±)-N-(3-aminopropyl)-N,N-dimethyl-2,3-bis(syn-9-tetradeceneyloxy)-1-propanaminium salts are preferred (U.S. Pat. No. 6,586,409).

The invention may also comprise combinations of aspects of one or more of the adjuvants identified above. For example, the following adjuvant compositions may be used in the invention: (1) a saponin and an oil-in-water emulsion (WO 99/11241); (2) a saponin (e.g., QS21)+a non-toxic LPS derivative (e.g. 3dMPL) (see WO 94/00153); (3) a saponin (e.g., QS21)+a non-toxic LPS derivative (e.g. 3dMPL)+a cholesterol; (4) a saponin (e.g., QS21)+3dMPL+IL-12 (optionally+a sterol) (WO 98/57659); (5) combinations of 3dMPL with, for example, QS21 and/or oil-in-water emulsions (see EP 0 835 318; EP 0 735 898; and EP 0 761 231); (6) SAF, containing 10% Squalane, 0.4% Tween 80, 5% pluronic-block polymer L121, and thr-MDP, either microfluidized into a submicron emulsion or vortexed to generate a larger particle size emulsion; (7) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (8) one or more mineral salts (such as an aluminum salt)+a non-toxic derivative of LPS (such as 3dPML); (9) one or more mineral salts (such as an aluminum salt)+an immunostimulatory oligonucleotide (such as a nucleotide sequence including a CpG motif).

Aluminum salts and MF59 are preferred adjuvants for use with injectable influenza vaccines. Bacterial toxins and bioadhesives are preferred adjuvants for use with mucosally-delivered vaccines, such as nasal vaccines.

3. Cationic Polysaccharides

Cationic polysaccharides for use in the invention include polysaccharides that have, or are capable of having (e.g., via protonation), one or more functional groups selected from suitable members of the following, among others: charged amino groups, including charged primary ($—NH_3^+$), secondary and tertiary amino groups, amidinium groups, guanidinium groups, triazolium groups, imidazolium groups, imidazolinium groups, pyridinium groups, sulfonium groups, including primary ($—SH_2^+$) and secondary sulfonium groups, hydrosulfide groups, phosphonium groups, including primary ($—PH_3^+$), secondary, and tertiary phosphonium groups, isothiouronium groups, nitrosyl groups, nitryl groups, tropilium groups, iodonium groups, antimonium groups, oxonium groups, and anilinium groups, among others.

In certain embodiments, the cationic polysaccharide contains multiple amino groups along its backbone and has a pKa ranging from 6 to 7. Consequently, only a fraction of the amino groups of these species are ionized at physiological pH.

Specific examples of amino-substituted cationic polysaccharides include cationic polysaccharides that comprise one or more aldosamine or ketosamine monomer units, for example, D-glucosamine monomer units. For instance, cationic polysaccharides are known, perhaps most notably chitosan, which comprise a combination of D-glucosamine and N-acetyl-D-glucosamine monomer units.

Chitosan in particular comprises randomly distributed β-(1-4)-linked D-glucosamine and N-acetyl-D-glucosamine monomer units, and is produced commercially by the alkaline N-deacetylation of chitin, which is a cellulose-like polymer consisting primarily of unbranched chains of N-acetyl-D-glucosamine. The degree of acetylation in commercial chitosans generally ranges from 60 to 70 to 80 to 90 to 100% although essentially any degree of acetylation is possible. Chitosan is biocompatible and biodegradable. Chitosan is positively charged in acidic to neutral solutions with a charge density dependent on the pH and the degree of deacetylation. The pKa value of chitosan generally ranges from 6.1 to 7.0, depending on the degree of deacetylation. Thus, while substantially insoluble in distilled water, chitosan is generally soluble in dilute aqueous acid (e.g., pH=6.5 or less). Chitosan is typically more soluble in organic acids (i.e. acetic acid) as compared to inorganic acids (i.e. hydrochloric acid). The molecular weight can vary widely (e.g., from less than 1,000 to 2,500 to 5,000 to 10,000 to 25,000 to 50,000 to 100,000 to 250,000 to 500,000 to 1,000,000 to 2,500,000 to 5,000,000 to 10,000,000 g/mole or more), with commercially available chitosan typically ranging from 100,000 to 1,200,000 g/mole in molecular weight. Specific examples of chitosan include those having a molecular weight ranging from less than or equal to 100,000 g/mole to 150,000 g/mole to 250,000 g/mole to 500,000 g/mole to 750,000 g/mole to 1,000,000 g/mole or more, a degree of deacetylation ranging from less than or equal to 60% to 75% to 85% to 95% or more, or a combination of both.

4. Microparticle Compositions

Useful polymers for forming the immunogenic microparticle compositions described herein include homopolymers, copolymers and polymer blends derived from the following: poly(α-hydroxy acids), polyhydroxy butyric acids, polylactones including polycaprolactones, polydioxanones and polyvalerolactone, polyorthoesters, polyanhydrides, polycyanoacrylates, tyrosine-derived polycarbonates and polyesteramides, among others. More typical are poly(α-hydroxy acids), such as poly(L-lactide), poly(D,L-lactide) (both known as APLA" herein), poly(hydroxybutyrates), copolymers of lactide and glycolide, such as poly(D,L-lactide-co-glycolides) (designated as "PLG" herein) or copolymers of D,L-lactide and caprolactone.

The above polymers are available in a variety of molecular weights, and the appropriate molecular weight for a given use is readily determined by one of skill in the art. Thus, for example, a suitable molecular weight for PLA may be on the order of about 2000 to 5000. A suitable molecular weight for PLG may range from about 10,000 to about 200,000.

Where copolymers are employed, copolymers with a variety of monomer ratios may be available. For example, where PLG is used to form the microparticles, a variety of lactide:glycolide molar ratios will find use herein, and the ratio is largely a matter of choice, depending in part on any coadministered adsorbed and/or entrapped species and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. Mixtures of microparticles with varying lactide:glycolide ratios may also find use herein in order to achieve the desired release kinetics. Degradation rate of the microparticles of the present invention can also be controlled by such factors as polymer molecular weight and polymer crystallinity.

PLG copolymers with varying lactide:glycolide ratios and molecular weights are readily available commercially from a number of sources including from Boehringer Ingelheim, Germany and Birmingham Polymers, Inc., Birmingham, Ala. Some exemplary PLG copolymers include: (a) RG 502, a PLG having a 50:50 lactide/glycolide molar ratio and a molecular weight of 12,000 Da; (b) RG 503, a PLG having a 50:50 lactide/glycolide molar ratio and a molecular weight of 34,000 Da; (c) RG 504, a PLG having a 50:50 lactide/glycolide molar ratio and a molecular weight of 48,000 Da, (d) RG 752, a PLG having a 75:25 lactide/glycolide molar ratio and a molecular weight of 22,000 Da; and (e) RG 755, a PLG having a 75:25 lactide/glycolide molar ratio and a molecular weight of 68,000 Da. PLG polymers can also be synthesized by simple polycondensation of the lactic acid component using techniques well known in the art, such as described in Tabata et al. (1988) *J. Biomed. Mater. Res.* 22:837-858.

Where used, poly(D,L-lactide-co-glycolide) polymers are typically those having a molar lactide/glycolide molar ratio ranging from 20:80 to 80:20, more typically 40:60 to 60:40, and having a molecular weight ranging from 10,000 to 100,000 Daltons, more typically from 20,000 Daltons to 70,000 Daltons.

Microparticles may be prepared using any of several methods well known in the art. For example, in some embodiments, double emulsion/solvent evaporation techniques, such as those described in U.S. Pat. No. 3,523,907 and Ogawa et al., *Chem. Pharm. Bull.* (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant.

In other embodiments, microparticles can also be formed using spray-drying and coacervation as described in, e.g., Thomasin et al. (1996) *J. Controlled Release* 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) *The A Wurster Process@ in Controlled Release Technologies: Methods, Theory, and Applications* (A. F. Kydonieus, ed.), Vol. 2, pp. 133-154 CRC Press, Boca Raton, Fla. and Deasy, P. B. (1988) *Crit. Rev. Ther. Drug Carrier Syst.* S(2):99-139; and ionic gelation as described by, e.g., Lim et al. (1980) *Science* 210:908-910.

In some embodiments, a water-in-oil-in-water (w/o/w) solvent evaporation system can be used to form the microparticles, as described by O'Hagan et al. (1993) *Vaccine* 11:965-969, O'Hagan et al. WO 00/06123, and Jeffery et al. (1993) *Pharm. Res.* 10:362-368.

In this method, a polymer of interest such as PLG is typically dissolved in an organic solvent, such as ethyl acetate, dimethylchloride (also called methylene chloride and dichloromethane), acetonitrile, acetone, chloroform, and the like. The polymer will typically be provided in about a 1-30%, more typically about a 2-15%, even more typically about a 3-10% and most typically, about a 4-8% solution w/v in organic solvent. The polymer solution is then combined with a first volume of an aqueous solution and emulsified to form an o/w emulsion. The aqueous solution can be, for example, deionized water, normal saline, a buffered solution, for example, phosphate-buffered saline (PBS) or a sodium citrate/ethylenediaminetetraacetic acid (sodium citrate/ETDA) buffer solution. The latter solutions can (a) provide a tonicity, i.e., osmolality, that is essentially the same as normal physiological fluids and (b) maintain a pH compatible with normal physiological conditions. Alternatively, the tonicity and/or pH characteristics of the compositions of the present invention can be optimized as desired for microparticle formation, and adjusted after microparticle formation as desired for administration. Preferably, the volume ratio of polymer solution to aqueous solution ranges from about 10:1 to about 2:1, more preferably about 5:1. Emulsification is conducted using any equipment appropriate for this task, and is typically a high-shear device such as, e.g., a homogenizer.

In some embodiments, one or more additional components are entrapped within the microparticles. For example, immunological species such as antigens and immunological adjuvants as well as other optional supplemental components such as those described below can be introduced by adding the same (a) to the polymer solution, if in oil-soluble or oil-dispersible form or (b) to the aqueous solution, if in water-soluble or water-dispersible form.

In some embodiments, the additional component (e.g., a negatively charged component such as a CpG oligonucletide, among others) is provided in the aqueous solution, complexed with one or more cationic polysaccharides. In these embodiments, the weight ratio of the cationic polysaccharide to the additional component can range, for example, from 0.0001:1 to 0.01:1 and the weight ratio of the cationic polysaccharide to the biodegradable polymer can range, for example, from 0.00005:1 to 0.005:1.

A volume of the o/w emulsion is then combined with a larger second volume of an aqueous solution, which can contain, for example, one or more cationic polysaccharides and/or one or more surfactants. The aqueous solution can be, for example, deionized water, normal saline, a buffered solution, for example, phosphate-buffered saline (PBS) or a sodium citrate/ethylenediaminetetraacetic acid (sodium citrate/ETDA) buffer solution, among other possibilities. The latter solutions can (a) provide a tonicity, i.e., osmolality, that is essentially the same as normal physiological fluids and (b) maintain a pH compatible with normal physiological conditions. Alternatively, the tonicity and/or pH characteristics of the compositions of the present invention can be optimized as desired for microparticle formation and adjusted after microparticle formation for administration. For example, the where chitosan is used as a cationic polysaccharide, the solution may contain 1% (vol/vol) acetic acid. In certain embodiments, the cationic polysaccharide and/or surfactant may be added to the above organic solution, instead of, or in addition to, the aqueous solution. The volume ratio of aqueous solution to o/w emulsion typically ranges from about 2:1 to 10:1, more typically about 4:1.

Where a cationic polysaccharide such as chitosan is supplied at this stage, it is typically provided in about a 0.1 to 1 w/w % solution, more typically about a 0.4 to 0.6 w/w % solution. A weight-to-weight polysaccharide-to-polymer ratio in the range of from about 0.0001:1 to about 0.1:1 is typically used, more typically from about 0.0005:1 to about 0.025:1, more typically from about 0.001:1 to about 0.01:1.

Where a cationic surfactant such as CTAB is supplied at this stage, it is typically provided in about a 0.00025-1% solution, more typically about a 0.0025-0.1% solution. Where an anionic surfactant such as DSS is used, it is typically provided in about a 0.00001-0.025% solution, more typically about a 0.0001-0.0025% solution. Where a nonionic surfactant such as PVA is used, it is typically provided in about a 2-15% solution, more typically about a 4-10% solution. For a cationic surfactant, a weight-to-weight surfactant-to-polymer ratio in the range of from about 0.00001:1 to about 0.5:1 is typically used; more typically from about 0.001:1 to about 0.1:1, and even more typically from about 0.0025:1 to about 0.05:1; for an anionic surfactant such as DSS, a weight-to-weight surfactant-to-polymer ratio in the range of from about 0.00001:1 to about 0.025:1 is typically used, more typically from about 0.0001:1 to about 0.0025:1; for a nonionic surfactant such as PVA a weight-to-weight surfactant-to-polymer ratio in the range of from about 0.001:1 to about 0.1:1 is typically used, more typically from about 0.0025:1 to about 0.05:1.

This mixture is then homogenized to produce a stable w/o/w double emulsion. Each of the above homogenization steps is typically conducted at a room temperature (i.e., 25° C.) or less, more typically less, for example, while cooling within an ice bath.

The formulation parameters can be manipulated to allow the preparation of small microparticles on the order of 0.05 μm (50 nm) to larger microparticles 50 μm or even larger. See, e.g., Jeffery et al. (1993) *Pharm. Res.* 10:362-368; McGee et al. (1996) *J. Microencap.* For example, reduced agitation typically results in larger microparticles, as do an increase in internal phase volume and an increase in polymer concentration. Small particles are typically produced by increased agitation as well as low aqueous phase volumes, high concentrations of emulsion stabilizers and a decrease in polymer concentration.

Organic solvents are then evaporated. Following preparation, microparticles can be used as is or lyophilized for future use.

Particle size can be determined as described above.

Upon preparation, a variety of components can be admixed with the microparticles, including immunological species such as antigens and immunological adjuvants as well as other optional supplemental components such as those described below, and the resulting formulation can be lyophilized prior to use if desired. Frequently, these components are added to the microparticles as an aqueous solution or dispersion. In some instances, these species will become adsorbed to the surface of the microparticles (see, e.g., the Examples below in which various species are adsorbed to the microparticle surface). The content of the adsorbed species can be determined using standard techniques.

The release properties of any adsorbed species may be characterized following lyophilization. For example, in certain embodiments, upon reconstitution of 10 mg of the lyophilized composition in 1 ml water, the compositions of the present invention can exhibit a release profile wherein 10% to 20% to 30% to 40% to 50% of the total amount of adsorbed immunological adjuvant is released from the microparticles beyond 15 days after reconstitution.

Thus, using techniques such as the above, among others, the polymer microparticles of the present invention may have a variety of components adsorbed thereon, as well as having a variety of components entrapped or encapsulated within them.

5. Supplemental Components

The immunogenic compositions of the present invention can include a wide variety of optional supplemental components. Such supplemental components include: (a) pharmaceuticals such as antibiotics and antiviral agents, nonsteroidal antiinflammatory drugs, analgesics, vasodilators, cardiovascular drugs, psychotropics, neuroleptics, antidepressants, antiparkinson drugs, beta blockers, calcium channel blockers, bradykinin inhibitors, ACE-inhibitors, vasodilators, prolactin inhibitors, steroids, hormone antagonists, antihistamines, serotonin antagonists, heparin, chemotherapeutic agents, antineoplastics and growth factors, including but not limited to PDGF, EGF, KGF, IGF-1 and IGF-2, FGF, (b) hormones including peptide hormones such as insulin, pro-insulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuroinedins, neurotensin, pancreastatin, pancreatic polypeptide, substance P, secretin, thymosin, and the like, (c) enzymes, (d) transcription or translation mediators, and (e) intermediates in metabolic pathways, among other components.

Such supplemental components can be, for example, adsorbed on the surface of the microparticles, entrapped within the microparticles, dissolved or dispersed in solution while unbound to the microparticles, adsorbed to or entrapped within another group of microparticles, and so forth.

5. Administration

Once formulated (and resuspended, if necessary), the microparticle compositions of the invention can be administered parenterally, e.g., by injection (which may be needleless). In this regard, the microparticle compositions may be supplied lyophilized in a vial or other container which is supplied with a septum or other suitable means for supplying a resuspension medium (e.g., Water for Injection) and for withdrawing the resultant suspension. A suitable syringe may also be supplied for injection.

The compositions can be injected subcutaneously, intradermally, intramuscularly, intravenously, intraarterially, or intraperitoneally, for example. Other modes of administration include nasal, mucosal, intraoccular, rectal, vaginal, oral and pulmonary administration, and transdermal or transcutaneous applications.

In some embodiments, the compositions of the present invention can be used for site-specific targeted delivery. For example, intravenous administration of the compositions can be used for targeting the lung, liver, spleen, blood circulation, or bone marrow.

The microparticle compositions of the present invention will generally include one or more pharmaceutically acceptable excipients. For example, vehicles such as water, saline, glycerol, polyethylene glycol, hyaluronic acid, ethanol, etc. may be used. Other excipients, such as wetting or emulsifying agents, biological buffering substances, and the like, may be present. A biological buffer can be virtually any solution which is pharmacologically acceptable and which provides the formulation with the desired pH, i.e., a pH in the physiological range. Examples include saline, phosphate buffered saline, Tris buffered saline, Hank's buffered saline, and the like. Depending on the final dosage form, other excipients known in the art can also be introduced, including binders, disintegrants, fillers (diluents), lubricants, glidants (flow enhancers), compression aids, colors, sweeteners, preservatives, suspending/dispersing agents, film formers/coatings, flavors and printing inks.

Treatment may be conducted according to a single dose schedule or a multiple dose schedule. A multiple dose schedule is one in which a primary course of administration may be given, for example, with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also be, at least in part, determined by the need of the subject and be dependent on the judgment of the practitioner.

Furthermore, if prevention of disease is desired, the compositions are generally administered prior to the arrival of the primary occurrence of the infection or disorder of interest. If other forms of treatment are desired, e.g., the reduction or elimination of symptoms or recurrences, the compositions are generally administered subsequent to the arrival of the primary occurrence of the infection or disorder of interest.

6. Kits

This invention encompasses kits which can simplify the administration of appropriate amounts of active ingredients to a subject. A typical kit of the invention comprises a unit dosage form of a composition of the invention, preferably in a sealed container. Kits of the invention can further comprise pharmaceutically acceptable vehicles that can be used to administer one or more active ingredients. For example, if a composition of the invention is provided in a solid form that must be reconstituted for administration, the kit further comprises a sealed container of a suitable vehicle in which the composition can be dissolved to form a particulate-free sterile solution that is suitable for administration, and a device that can be used to administer the active ingredient. Examples of such devices include, but are not limited to, syringes, drip bags, patches, and inhalers.

C. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Microparticle Preparation

Comparative biodegradable microparticles were created by solvent evaporation methods analogous to those previously established for anionic particles (Singh, M. et al. (2004) *J. Pharm. Sci.* 93 (2):273-282) and for cationic particles (Singh, M., et al. (2000) *Proc. Natl. Acad. Sci. USA* 97 (2): 811-816). More particularly, a water/oil/water emulsion technique was used to prepared the poly(lactide-co-glycolide) (PLG) microparticles. The anionic particles were prepared with 0.05% dioctyl sodium sulfosuccinate (DSS) available from Sigma Chemicals, St. Louis, Mo., USA, and the cationic particles were prepared with 1% (wt/wt) cetyltrimethylammonium bromide (CTAB) available from Sigma in the external aqueous phase.

PLG, i.e., RG503, a PLG Polymer having a 50:50 lactide/glycolide molar ratio and a molecular weight of ~30 kDaltons, available from Boehringer Ingelheim, was dissolved in dichloromethane (6% wt/vol) and added to a phosphate buffered saline aqueous phase (1:5 water:oil) (10 ml combined with 50 ml) and homogenized for 2 minutes using a 10-mm probe of a homogenizer (Ultra-Turrax T25 IKA-Labortechnik, Germany) at 15,000 rpm. This water-in-oil emulsion was then added to 250 ml of water containing the anionic or cationic and homogenized at high speed using a 45-mm probe of a homogenizer (Ultra-Turrax T50 IKA-Labortechnik, Germany, for 20 minutes. The suspension was stirred with magnetic stirring to allow the solvent to evaporate.

Chitosan-containing microparticles in accordance with the invention were formed using the procedures as set forth above, except that the 250 ml aqueous phase in the second emulsification step was formed by the addition of chitosan stock solution, available from Sigma, 5 mg/ml, dissolved in acetic acid, to water. The chitosan was added in an amount sufficient to yield the appropriate ratio (i.e., 0.1% to 1% w/w PLG). The amount of acetic acid was sufficient to bring the pH of the 250 mL aqueous phase to a pH of 5.0-5.5. Stable particles were formed with chitosan concentrations varying from 0.25% (wt/wt relative to PLG) up to 1.0% (wt/wt). A relatively low molecular weight chitosan (average MW=150, 000 g/mole, degree of deacetylation=75%-85%) available from Sigma was used for all the experiments described here.

Another less soluble, higher molecular weight chitosan (MW=600,000 g/mole, degree of deacetylation 75%-85%) available from Sigma was also used to form stable particles, which have properties very similar to those formed with the low molecular weight chitosan. Attempts at forming particles with chitosan chloride (which is freely soluble in water, forming viscous solutions and eventually becoming a paste at higher concentrations), did not yield a stable emulsion. More particularly, these compounds did not function as emulsion stabilizers, apparently because they did not accumulate in significant amounts at the oil-water interface due to their high solubility.

The size distribution of the resulting microparticles was determined using a particle size analyzer (Horiba LA-930, Irvine, Calif.).

Zeta potential was measured with the Zetasizer (Zetasizer 3000HSA Malvern Instruments, UK) with the sample diluted in buffers ranging from pH 4 to pH 7.

Percent chitosan associated with the pellet was determined by a ninhydrin-hydrindantin assay, adapted to a 96 well plate format (see, Prochazkova, S. "Quantitative determination of chitosans by ninhydrin" *Carbohydrate Polymers* 38:115-122).

Properties of the above particles are summarized in Tables 1A and 1B.

TABLE 1A

COMPARISON OF MICROPARTICLE PROPERTIES

| | Size (μm) | | Zeta | % Chitosan |
|---|---|---|---|---|
| | D(v, 0.5) | D(v, 0.9) | (mV) | on pellet |
| 0.25% (wt/wt) chitosan | 4.1 | 8.06 | +49 | 64 |
| 0.5% (wt/wt) chitosan | 2.9 | 5.8 | +49 | 22 |
| 1.0% (wt/wt) chitosan | 2.2 | 4.9 | +49 | 13 |

TABLE 1B

COMPARISON OF MICROPARTICLE PROPERTIES

| | Size (μm) | | |
|---|---|---|---|
| | D(v, 0.5) | D(v, 0.9) | Zeta (mV) |
| 0.25% (wt/wt) chitosan | 4.2 | 9.8 | +49 |
| 0.5% (wt/wt) chitosan | 2.7 | 5.1 | +49 |
| 0.5% (wt/wt) DSS | 0.8 | 1.2 | −13 |
| 1% (wt/wt) CTAB | 0.8 | 1.2 | +30 |

Example 2

CPG Oligonucleotide Adsorption and Release

The CpG oligonucleotide is a potent adjuvant and its co-delivery with microparticles offers expanded formulation options.

Soluble CpG solution (see Example 7) was added to the microparticle suspension of Example 1 and was agitated on a lab rocker at 4° C. overnight. The microparticles were separated by centrifugation. The amount remaining in the supernatant (not adsorbed) was determined by UV spectroscopy, absorbance at 260 nm.

FIG. 1 compares release profiles of the adsorbed CpG for the three different particle types. The CpG has a slow release from the chitosan-PLG particles, while it is 100% released (equivalent to no CpG adsorption) from the DSS-PLG particles and is essentially all immediately released from the CTAB-PLG particles.

The adsorption and release of CpG to and from the chitosan-PLG particles also varies with the amount of chitosan associated with the PLG microparticles. See Table 2. As the concentration of chitosan increases, the amount of CpG released from the particles decreases. For 1% chitosan-PLG, there was very little CpG released, even after 1 week.

TABLE 2

1% CPG ADSORPTION TO CHITOSAN PARTICLES
WITH INCREASING CHITOSAN CONCENTRATION

| | % Release | | |
|---|---|---|---|
| | 2 hours | 24 hours | 1 week |
| 0.25% (wt/wt) chitosan | 50 | 82 | 90 |
| 0.5% (wt/wt) chitosan | 46 | 63 | 71 |
| 1.0% (wt/wt) chitosan | 1 | 2 | 2 |

Example 3

Polysaccharide Adsorption to Particles

An oligosaccharide from Meningococcal C (MenC) (Chiron Vaccines (IRIS, Chiron, S.r.l., Siena, Italy); described in P. Costantino et al. (1992) *Vaccine* 10: 691-698) was investigated for its adsorption to the particles. MenC was added to the microparticle suspension of Example 1 and was agitated on a lab rocker at 4° C. overnight. The concentration of the polysaccharide was determined by a modified Svennerholm method (see *Biochem. Biophys. Acta* (1957) 24:604) for the detection of sialic acid.

The suspension was lyophilized and in vitro release was determined with 1 mL of distilled water, rocked at 25° C. for 1 hour or longer. The microparticles were separated by centrifugation and the pellets were hydrolyzed with 0.2 N NaOH overnight. The concentration of sialic acid in the supernatant and pellet was measured to determine the release of MenC.

At a target load of 0.5% (wt/wt PLG), the MenC adsorbs at almost 100% efficiency to the 0.5% chitosan-PLG microparticles and at 70% efficiency to the 0.25% chitosan-PLG, whereas the MenC adsorbs to the DSS-PLG particles with low efficiency. See Table 3. As the target MenC load increases, the adsorption efficiency to the chitosan-PLG particles decreases, with a sharper reduction for the lower concentration chitosan-PLG particles.

TABLE 3

MENC OLIGOSACCHARIDE ADSORPTION TO PLG
MICROPARTICLES WITH INCREASING LOADS

| | % Adsorption for various MenC target adsorption loads (% wt/wt PLG) | | | | |
|---|---|---|---|---|---|
| | 0.1% | 0.2% | 0.5% | 1.0% | 2.0% |
| 0.25% (wt/wt) chitosan | 99.7 | 96.9 | 68.5 | 42.3 | 30.7 |
| 0.5% (wt/wt) chitosan | 96.9 | 98.7 | 96.9 | 83.6 | 45.6 |
| 0.05% (wt/wt) DSS | 11.3 | 12.6 | 10.2 | — | — |

Figure 2:
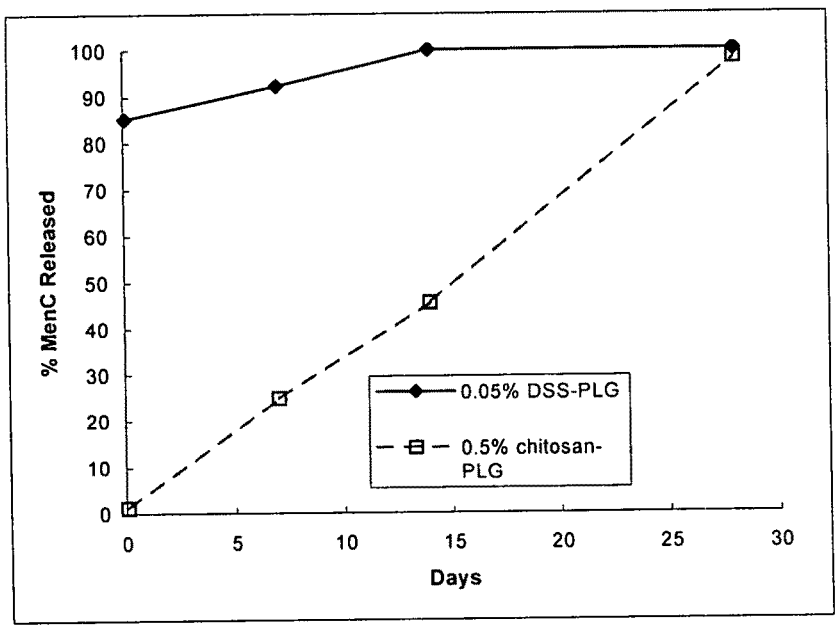
FIG. 2 is a plot of MenC polysaccharide release over 28 days for varying particle types with an initial target load of 0.5% adsorbed MenC wt/wt relative to PLG.

As seen from FIG. 2, the release profile shows a steady release of the MenC from the 0.5% chitosan-PLG particles, while all the MenC is essentially immediately released from the DSS-PLG particles.

Example 4

Protein Adsorption to Particles

The chitosan-PLG microparticles can also be used to adsorb proteins. Meningococcal B protein MB961 (Chiron Vaccines, (IRIS, Chiron, S.r.l., Siena, Italy); described in Pizza et al. (2000) *Science* 287: 1816-1820) was added to the microparticle suspension of Example 1 and agitated on a lab rocker at 4° C. overnight. The microparticles with adsorbed protein were separated by centrifugation, and the amount of unbound protein remaining in the supernatant was measured by Gel filtration chromatography. Essentially, 100 µl of the supernatant was injected on a TSK3000SWXL (TOSOH Bioscience, Japan) with a Waters 2690/432 instrument (Bedford, Mass.). Linear calibration curves were established in the range of 10-200 µg/ml with Men B protein, and the amount of protein present in the supernatant was calculated. The total amount of unbound protein was then subtracted from the total amount of protein added initially and the difference was used to calculate the actual loading efficiency.

As seen from Table 4, the protein MB961 adsorbs with much higher efficiency to the chitosan-PLG particles as compared to the DSS-PLG particles.

TABLE 4

MB961 PROTEIN ADSORPTION EFFICIENCY
TO DIFFERENT PARTICLE TYPES AT A TARGET
LOAD OF 1% (WT PROTEIN/WT PLG)

| | % Adsorbed (pre-lyophilization) | % Released (post-lyophilization) |
|---|---|---|
| 0.25% (wt/wt) chitosan | 100 | 10 |
| 0.05% (wt/wt) DSS | 40 | 53 |

Example 5

Preparation of Anionic Microparticles

Anionic PLG microparticles for protein adsorption were prepared using a solvent evaporation technique. Briefly, the microparticles were prepared by emulsifying 30 mL of a 6% w/v polymer (RG503) solution in methylene chloride with 6 mL of PBS at high speed using an IKA homogenizer. The primary emulsion was then added to 144 mL of distilled water containing DSS (0.6% w/v) and homogenized using an Omni homogenizer. This resulted in the formation of a w/o/w emulsion, which was stirred for 12 h at room temperature, allowing the methylene chloride to evaporate.

Example 6

Adsorption of Men B 287 to Anionic Microparticles

*Escherichia coli*-derived recombinant *Neisseria meningitidis* serotype B vaccine candidate, Men B 287 (Chiron Vaccines (IRIS, Chiron, S.r.l., Siena, Italy); described in Pizza et al. (2000) *Science* 287: 1816-1820) was used in this example.

To prepare microparticles with adsorbed proteins, a microparticle suspension containing 100 mg of PLG from Example 5 was incubated with 1 mg of Men B 287 in a 10-mL total volume. The suspension was then agitated on a lab rocker (Aliquot Mixer, Miles Laboratories) at 4° C. overnight. Sugars (45 mg/ml of mannitol and 15 mg/ml of sucrose) were added and aliquots of the suspension (2 µg or 10 µg or 20 µg Men B 287/animal) were then placed into small glass vials and lyophilized "PLG/287 2 µg vial," or "PLG/287 10 µg vial" or "PLG/287 20 µg vial").

Example 7

Soluble CpG

A CpG oligonucleotide, 5'-TCC ATG ACG TTC CTG ACG TT-3' (SEQ ID NO. 1), was synthesized with a phosphorothioate backbone by Oligos Etc. (Wilsonville, Oreg., 99% purity by HPLC) and supplied in a lyophilized form. It was suspended in 10 mM Tris (pH 7.0) 1 mM EDTA and stored at −80° C. ("soluble CpG solution").

Example 8

Preparation of Charged Microparticles with Encapsulated CpG

Anionic PLG microparticles with 50% encapsulated CpG were prepared using a solvent evaporation technique. Briefly, the microparticles were prepared by emulsifying 5 mL of a 12% w/v polymer solution in methylene chloride with 0.700 mL of TE and 0.300 ml of CpG-Chitosan Complex at high speed using an IKA homogenizer. The CpG-Chitosan complex was prepared by adding Chitosan solution, 2.2 mg/mL chitosan in 1% (vol/vol) acetic acid to the soluble CpG solution described in Example 7 in a 1:1000 ratio w/w, respectively. The amount of CpG used in the microparticle formulation was 0.5% w/w relative to PLG. The primary emulsion was then added to 32 mL of distilled water containing DSS (0.9% w/v) and homogenized using an Omni homogenizer. This resulted in the formation of a w/o/w emulsion, which was stirred for 12 h at room temperature, allowing the methylene chloride to evaporate. Sugars (45 mg/ml of mannitol and 15 mg/ml of sucrose) were added and aliquots of the suspension (10 µg CpG/animal) were then placed into small glass vials and lyophilized ("PLG/CpGEncap 50% vial").

The process for 100% encapsulated CpG was similar to the above with the exception of Chitosan:CpG ratio changed to 1:1.4 w/w respectively lyophilized ("PLG/CpGEncap 100% vial").

Microparticles with a target of 50% encapsulated CpG were also formed using PVA (M.W. 15,000 from ICN Biomedicals, Aurora, Ohio) as a viscosity imparting agent. Microparticles were made as above by mixing CpG and PVA solution [0.5% CpG w/w PLG and 7.5% PVA w/w PLG] and adding the mixture to the water phase prior to homogenization. Encapsulation efficiency plateaued at 50% with this approach.

Encapsulation/adsorption efficiency of CpG in the microparticles was evaluated as follows. The PLG/CpG microparticles were hydrolyzed using 1N Sodium Hydroxide and the samples read by UV absorption at 260 nm to yield the load of CpG. The PLG/CpG microparticles were centrifuged and the supernatants were separated and detected by uv absorption at 260 nm. The difference of CpG in the supernatant and the CpG load gave the encapsulation/adsorption efficiency.

As indicated above, an encapsulation efficiency of 50% (0.5% target load w/w PLG) was obtained with a ratio of 1000:1 for CpG and Chitosan complexation. Efforts were made to increase the encapsulation efficiency of CpG, and CpG and Chitosan complexed at a ratio of 1.4:1 was found to yield a white precipitate. The complex was centrifuged and an analysis of the supernatant showed the absence of CpG and Chitosan indicating the total complexation of CpG and Chitosan. Moreover, CpG appeared to remain in the particles during overnight protein adsorption (see below). Neither molecule (neither CpG nor chitosan) appeared to partition into the aqueous phase as was determined by HPLC assay performed following protein adsorption. This is believed to be due to the fact that these molecules are complexed with Chitosan, and tend to predominantly remain within the microparticles.

Example 9

CpG Oligonucleotide Release

Figure 5:
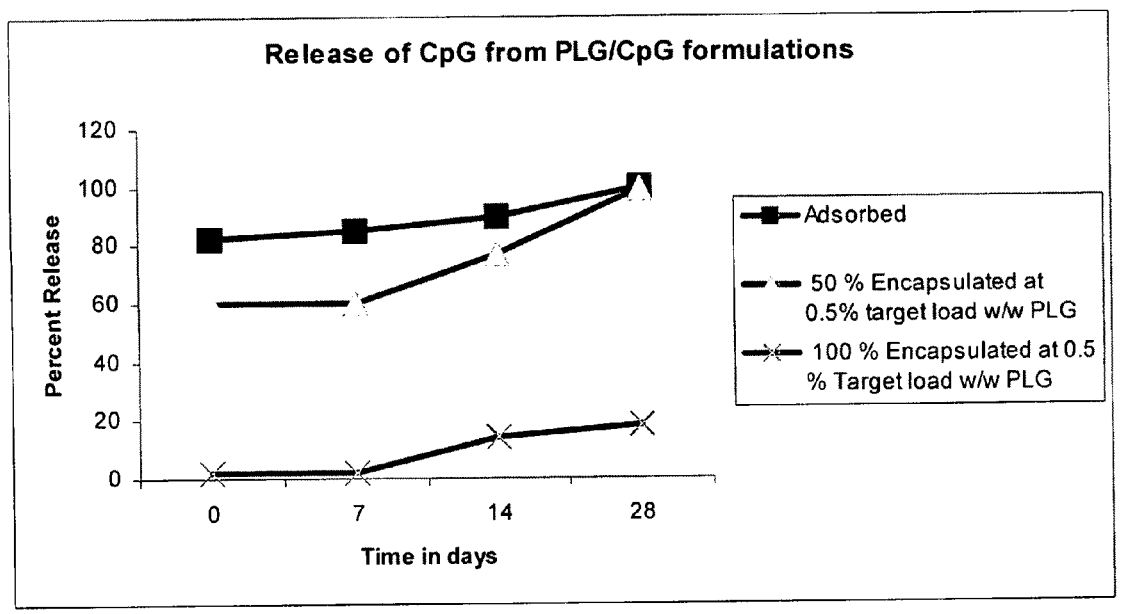
FIG. 5 is a plot of CpG release over 28 days comparing adsorbed and encapsulated formulations having an initial target load of 1.0% CpG w/w PLG for adsorbed formulation and 0.5% CpG wt/wt relative to PLG for encapsulated formulations.

In vitro release profiles were measured for three microparticle formulations (FIG. 5). In a first formulation, Water for injection was added to reconstitute CTAB-PLG microparticles with CpG adsorbed (i.e., CTAB-PLG microparticles from Example 1, 1% target load w/w PLG and agitated on a lab rocker at 4 deg C. overnight) and referred to hereinafter as "adsorbed". In a second formulation, Water for injection was added to reconstitute PLG microparticles with CpG ("PLG/CpGEncap 50% vial") from Example 8 (0.5% target load w/w PLG) and (referred to hereinafter as "50% encapsulated at 0.5% target load w/w PLG"). In a third formulation, Water for injection was added to reconstitute PLG microparticles with CpG ("PLG/CpGEncap 100% vial") from Example 8 (0.5% target load w/w PLG) and (referred to hereinafter as "100% encapsulated at 0.5% target load w/w PLG"). CpG release was measured for each formulation at 0, 7, 14 and 28 days. For release measurement, the microparticles were separated by centrifugation, and the amount of CpG remaining in the supernatant (not associated with PLG microparticles) was determined by uv spectroscopy, absorbance at 260 nm.

FIG. 5 compares the release profiles of the CpG for the three different particle types. The "adsorbed" formulation had the fastest release, the "100% encapsulated at 0.5% target load w/w PLG" formulation had the slowest release, and the "50% encapsulated at 0.5% target load w/w PLG" formulation had an intermediate release. Moreover, the adsorbed formulation had about 80-85% release at time zero. CpG formulations with an initial 50% encapsulation released the CpG gradually with total release achieved over a period of four weeks. The CpG formulation, which had about 100% encapsulation, did not release the CpG even at the end of six weeks yielding a flat release profile.

Example 10

Further Release Studies

PLG/DSS microparticles were prepared and characterized as described in D. O'Hagan, M. Singh, Microparticles as vaccine adjuvants and delivery systems, Expert Review Vaccines 2 (2003) 269-283. As in Example 1 CpG release was evaluated as in Example 8 above. Protein adsorption was evaluated as in Example 4 above.

The results obtained are presented in Table 5. Adsorption of Men B protein to PLG microparticles was highly efficient at 89-99% of target load. Initial CpG release was consistent with that expected for the 50% and 100% encapsulated CpG microparticles. Release was higher for the PLG microparticles with adsorbed CpG.

TABLE 5

ADSORPTION EFFICIENCY OF MEN B FORMULATED AND INITIAL RELEASE OF CPG WITH ANIONIC PLG MICROPARTICLES WITH AND WITHOUT ENCAPSULATED CPG.

| Formulation | Target load % w/w* | % adsorption efficiency of Men B$^\Psi$ | % Initial Release of CpG$^\#$ |
|---|---|---|---|
| PLG/Men B | 1 | 99 | — |
| PLG/Men B + PLG/CpG Adsorbed | 1 | 99 | 82 |
| PLG/Men B + PLG/Chitosan – CpG Encapsulated 50% | 1 | 99 | 60 |
| PLG/Chitosan – CpG Encapsulated/Men B 100% | 1 | 99 | 2 |

*Target load is based on weight of protein to weight of polymer
$^\Psi$Adsorption efficiency is calculated as % of target load adsorbed
$^\#$Initial Release calculated as % of Load obtained

Example 11

Integrity of Adsorbed Protein

Adsorbed proteins were evaluated for integrity by SDS PAGE analysis, Western Blot and HPLC assays. The proteins were extracted from 10 mg microparticles, with or without entrapped CpG [Examples 1 and 4], with 200 μl of SDS sample buffer, and 30 μl was loaded on a 4-20% gradient Tris/glycine polyacrylamide gel (Novex, San Diego, Calif.) for SDS PAGE analysis. The gel was stained with Colloidal blue stain (Novex), de-stained, and dried.

The integrity of proteins adsorbed to microparticles was found to be well-preserved following lyophilization. Protein extracted from microparticles and run on SDS-PAGE were identical in molecular weight to proteins before adsorption with no apparent aggregation or degradation (data not shown). Moreover, the presence of CpG in microparticles did not seem to affect the integrity of Men B protein adsorbed on the surface. This is an important aspect of vaccine formulation. For a vaccine to induce functional antibodies and a potent immune response, it needs to contain intact antigens. In the past decade, it has been more common to deliver antigens encapsulated in PLG microparticles; however, this approach suffers from the adverse effects of the encapsulation process on the integrity of protein. D. T. O'Hagan, *Prospects for the development of new and improved vaccines through the use of microencapsulation technology*, New Generation Vaccines; Marcel Dekker, Inc.: New York, (1997) pp 215-228. H. Okada, H. Toguchi, *Biodegradable microspheres in drug delivery*, 12 (1995) 1-99. We have previously demonstrated that delivering antigens adsorbed on the surface of microparticles results in a much more potent immune response compared to entrapped antigens. J. Chesko et al., *Pharm Res.* 2004 December; 21 (12): 2148-52.

Example 12

In Vivo Studies

For group 1 ("PLG/287, 2 μg") and group 4 ("PLG/287, 20 μg") in Table 6 below, PLG/287 vials containing 2 μg and 20 μg Men B 287 (i.e., the PLG/287 2 μg and PLG/287 20 μg vials of Example 6), respectively, were reconstituted with Water for Injection at the time of immunization. For group 2 (PLG/287+soluble CpG, 2 μg) and group 5 (PLG/287+soluble CpG, 20 μg), the PLG/287 vials, 2 μg and 20 μg Men B 287 per animal (from Example 6), respectively, were reconstituted with Water for Injection and soluble CpG was added (10 μg per animal) at the time of immunization. For group 3 (PLG/287+PLG/0.5% Chitosan/CpG encapsulated, 2 μg), vials of the PLG/287 (2 μg Men B 287 per animal) (from Example 6) and the PLG with encapsulated CpG (CpGEncap) (10 μg CpG/animal) (i.e., the PLG/CpGEncap 50% vial of Example 8) were reconstituted with Water for Injection and mixed together at the time of immunization. For group 6 (PLG/287+PLG/0.5% Chitosan/CpG encapsulated, 20 μg), vials of the PLG/287 (20 μg Men B 287 per animal) (from Example 6) and the PLG with encapsulated CpG (CpGEncap) (10 μg CpG/animal) (from Example 8) were reconstituted with Water for Injection and mixed together at the time of immunization.

For all groups, samples were injected IM into groups of 10 female CD-1 mice on day(s) 0, 21 and 35. At day 39 and day 56, serum ELISA titers were analyzed as described in Singh, M. et al. (2004) *J. Pharm. Sci.* 93 (2):273-282. Enzyme-linked immunosorbent assay (ELISA) microtiter plates were obtained from Nunc, Denmark. At day 56 serum bactericidal activity (SBA) was analyzed as described in Pizza, M. et al. (2000) *Science* 287 (5459): 1816-1820. 2996 is the strain of MenB used for SBA analysis. The SBA assay measures the ability of antibody to fix complement on the surface of the bacterium and trigger bacterial lysis. For detection of TH1- and TH2-type cytokine responses, single cell suspensions from spleens (SP) collected from individual animals were cultured for 17 hours in 96 well plates at a concentration of 1 million cells per well in the presence or absence of the MenB recombinant protein at a final concentration of 10 μg/ml and 2.5 μg/ml anti-mouse CD28 antibody (BD). Supernatants were collected and stored at −80° C. The Multiplex Luminex assay was performed with 50 μl of supernatants for simultaneous detection of the cytokines according to manufacturers protocol (Millipore).

Figure 3:
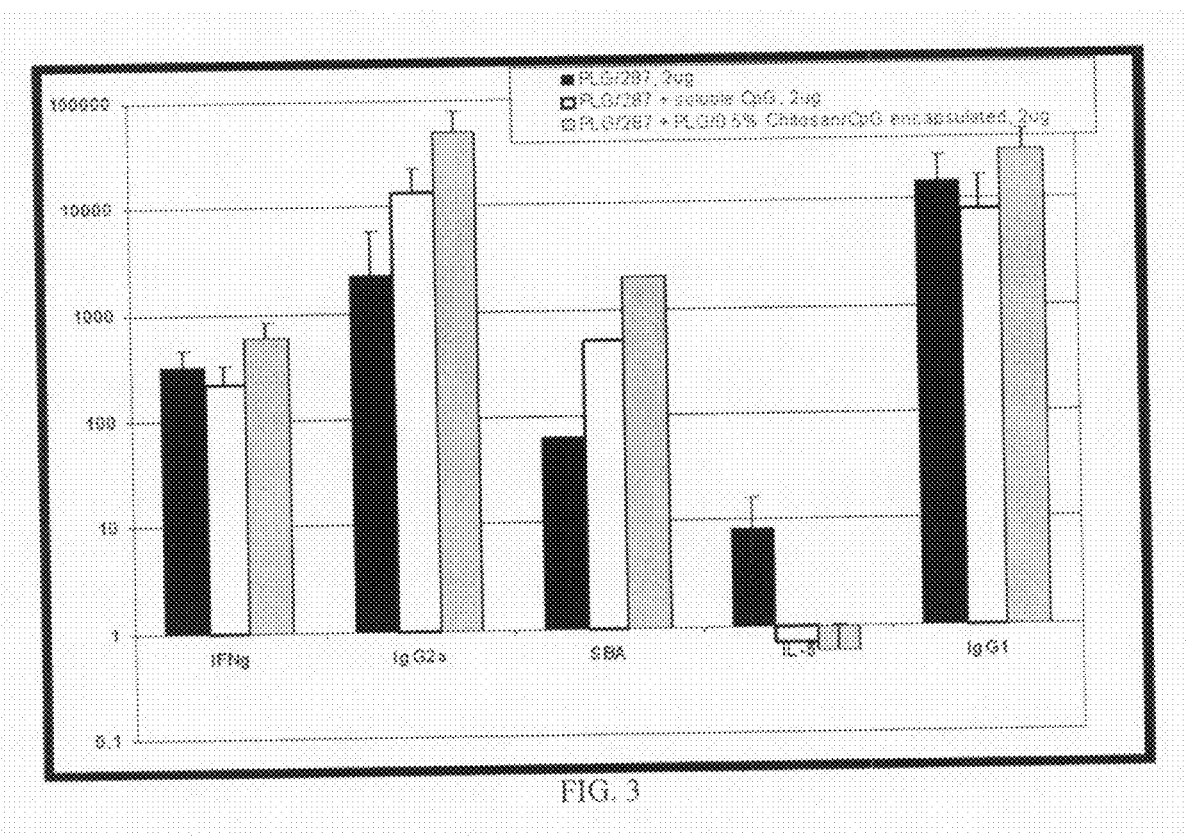
FIGS. 3 and 4 depict immune responses for mice vaccinated with microparticle formulations loaded with Men B 287 protein (2 or 20 µg), either without CpG oligonucleotide, with soluble CpG oligonucleotide, or with entrapped CpG oligonucleotide.
Figure 4:
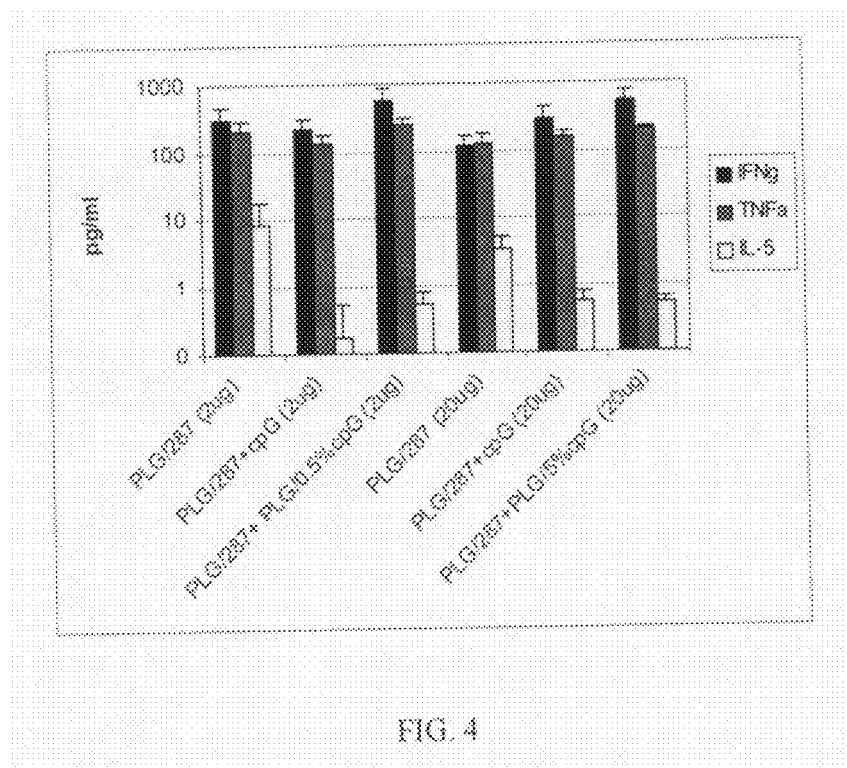

The results are presented in Table 6 and in FIGS. 3 and 4. [See new FIG. 4] As seen from FIGS. 3 and 4, entrapment of CpG in PLG, designated "PLG/287+PLG/0.5% Chitosan/CpG encapsulated, 2 μg" in FIG. 3 and designated "PLG/287+PLG/0.5% CpG (2 μg)" or "PLG/287+PLG/0.5% cpG (20 μg)" in FIG. 4, significantly enhanced IFN-γ (IFNg) and TNF-α (TNFa) responses against co-administered adsorbed Men B 287, versus adsorbed Men B 287 alone and adsorbed Men B 287 with soluble CpG. The antibody titers (IgG), Table 6 also show that the "PLG/287+PLG/0.5% Chitosan/CpG encapsulated" groups (2 μg or 20 μg) have enhanced responses versus adsorbed Men B 287 alone and adsorbed Men B 287 with soluble CpG. Adsorbed PLG-287 (2 μg) alone, without soluble or entrapped CpG, induced significantly enhanced IL-5 responses. Relatively low IL-13 responses were detectable and the data are not shown. CpG has been shown to increase TH I-type cytokine responses, while decreasing TH2-type cytokine responses, IFNγ and TNFα, as well as IL-5 and IL-13, which are well established TH1 and TH2 type cytokines, respectively, were measured.

TABLE 6

| Group | Formulation | Route | IgG (GMT) Day 39 |
|---|---|---|---|
| 1 | PLG/287, 2 µg | IM | 904 |
| 2 | PLG/287 + soluble CpG, 2 µg | IM | 2,908 |
| 3 | PLG/287 + PLG/0.5% Chitosan/CpG encapsulated, 2 µg | IM | 8,606 |
| 4 | PLG/287, 20 µg | IM | 2,765 |
| 5 | PLG/287 + soluble CpG, 20 µg | IM | 16,577 |
| 6 | PLG/287 + PLG/0.5% Chitosan/CpG encapsulated, 20 µg | IM | 32,770 |

Example 13

In Vivo Studies

For group 1 (PLG/Men B 2 µg) in Table 7 below, a PLG/287 vial containing 2 µg Men B 287 (i.e., the PLG/287 2 µg vial of Example 6) was reconstituted with Water for Injection at the time of immunization. For group 2 (PLG/Men B 2 µg+soluble CpG) a vial of the PLG/287 (2 µg Men B 287 per animal, from Example 6) was reconstituted with Water for Injection and soluble CpG was added (10 µg per animal) at the time of immunization. For group 3 (PLG/Men B 2 µg+PLG/CTAB/CpG Adsorbed), a vial of the PLG/287 (2 µg Men B 287 per animal, from Example 6) was reconstituted with Water for Injection and CTAB-PLG microparticles with CpG adsorbed (see Example 9) was added at the time of immunization. For group 4, (PLG/Men B 2 µg+Chitosan/CpG 50% Encapsulated), vials of the PLG/287 (2 µg Men B 287 per animal) (from Example 6) and the PLG with encapsulated CpG (CpGEncap) (10 µg CpG/animal) (i.e., the PLG/CpG 50% Encap vial of Example 8) were reconstituted with Water for Injection and mixed together at the time of immunization.

For all groups, samples were injected IM into groups of 10 female CD-1 mice on day(s) 0, 21 and 35. At day 49 (two weeks post third immunization), serum ELISA titers were analyzed as described in Singh, M. et al. (2004) *J. Pharm. Sci.* 93 (2):273-282, and serum bactericidal activity (SBA) was analyzed as described in Pizza, M. et al. (2000) *Science* 287 (5459): 1816-1820. 2996 is the strain of MenB used for SBA analysis.

The results are presented in Table 7. As seen from Table 7, adding CpG in adsorbed form, using Chitosan for forming cationic PLG microparticles, did not have any significant improvement over adding CpG in Soluble form. A similar trend was observed with bactericidal activity. CpG encapsulated, using Chitosan as a complexing agent, in PLG microparticles with *Neisseria meningitides* B adsorbed on separate PLG microparticles and coadministered, showed greater than three-fold enhancement of antibody titers and bacteriocidal titers when compared with Soluble CpG group at the 2 µg dose. These data demonstrate that encapsulating CpG can be used to improve the immune response to vaccine antigens. Not only were Men B-specific antibody titers significantly increased, but also more importantly, the production of functional antibodies was greatly enhanced as measured by complement-mediated bactericidal activity in serum, which is a reliable correlate of protective efficacy for Men B vaccines. M. Pizza et al., *Science* 287 (2000) 1816-1820 and R. A. Wall, Meningococcal disease: treatment and prevention, Ann. Med. 34 (2002) 624-634.

TABLE 7

THE ADJUVANT EFFECT OF CPG ON THE INDUCTION OF ANTIBODY RESPONSES AGAINST MEN B PROTEIN 2 µG DOSE$^\alpha$

| Group | Formulation | Anti-Men B serum IgG titers | Anti-Men B serum IgG$_{2a}$ titers | Bactericidal activity (SBA) |
|---|---|---|---|---|
| 1 | PLG/Men B 2 µg | 2007 | 977 | 64 |
| 2 | PLG/Men B 2 µg + CpG Soluble | 5992 | 16,250 | 512 |
| 3 | PLG/Men B 2 µg + PLG/CTAB/CpG Adsorbed | 5900 | 9715 | 512 |
| 4 | PLG/Men B 2 µg + PLG/Chitosan-CpG 50% Encapsulated | 20,788 | 44,275 | 2,048 |

Example 14

In Vivo Studies

For group 1 (PLG/Men B 10 µg) in Table 8 below, a PLG/287 vial containing 10 µg Men B 287 (i.e., the PLG/287 10 µg vial of Example 6) was reconstituted with Water for Injection at the time of immunization. For group 2 (PLG/Men B 10 µg+soluble CpG) a vial of the PLG/287 (10 µg Men B 287 per animal, from Example 6) was reconstituted with Water for Injection and soluble CpG was added (10 µg per animal) at the time of immunization. For group 3 (PLG/Men B 10 µg+CpG/Chitosan), a vial of the PLG/287 (10 µg Men B 287 per animal, from Example 6) was reconstituted with Water for Injection and Chitosan—CpG complex was added at the time of immunization (CpG 10 µg per animal was complexed with Chitosan in the ratio of 1.4:1 respectively). For group 4, (PLG/Men B 10 µg+Chitosan/CpG 100% Encapsulated), vials of the PLG/287 (10 µg Men B 287 per animal) (from Example 6) and the PLG with encapsulated CpG (CpGEncap) (10 µg CpG/animal) (i.e., the PLG/CpG 100% Encap vial of Example 8) were reconstituted with Water for Injection and mixed together at the time of immunization. For group 5 (PLG/Men B 10 µg+Chitosan/CpG 50% Encapsulated), vials of the PLG/287 (10 µg Men B 287 per animal) (from Example 6) and the PLG with encapsulated CpG (CpGEncap) (10 µg CpG/animal) (i.e., the PLG/CpGEncap vial of Example 8) were reconstituted with Water for Injection and mixed together at the time of immunization.

For all groups, samples were injected IM into groups of 10 female CD-1 mice on day(s) 0, 21 and 35. At day 49 (two weeks post third immunization), serum ELISA titers were analyzed as described in Singh, M. et al. (2004) *J. Pharm. Sci.* 93 (2):273-282, and serum bactericidal activity (SBA) was analyzed as described in Pizza, M. et al. (2000) *Science* 287 (5459): 1816-1820. 2996 is the strain of MenB used for SBA analysis.

The results are presented in Table 8. As seen from Table 8, encapsulating CpG with about 100% encapsulation efficiency inside microparticles enhanced the response over that obtained with soluble CpG with respect to antibody titers. The CpG-Chitosan complex group showed lesser or comparable responses to Soluble CpG. This demonstrates the importance of encapsulating CpG-Chitosan complex in PLG microparticles. However, the IgG$_{2a}$ titers and the serum bactericidal titers of the encapsulated formulations at the 10 µg dose did not exhibit a statistically significant effect, with only the 50% encapsulated formulation showing a two fold increase in serum bactericidal titers. This result is different from the results observed at 2 µg Men B 287 dose, which emphasizes the significance of Men B 287 dose selection, as a plateau effect can be observed starting at 10 µg antigen dose. In mice, the production of the IgG$_{2a}$ antibody isotype is widely recognized as characteristic of a Th1 response. See, e.g., C. M. Snapper, *Science* 236 (1987) 944-947.

TABLE 8

ADJUVANT EFFECT OF CPG ON THE ANTIBODY RESPONSES AGAINST MEN B PROTEIN 10 µG

| Group | Formulation | Anti-Men B serum IgG titers | Anti-Men B serum IgG$_{2a}$ titers | Bactericidal activity (SBA) |
|---|---|---|---|---|
| 1 | PLG/Men B 10 µg | 10,830 | 1860 | 128 |
| 2 | PLG/Men B 10 µg + soluble CpG | 16,820 | 41,725 | 2048 |
| 3 | PLG/Men B 10 µg + CpG/Chitosan | 17,683 | — | 2048 |
| 4 | PLG/Men B 10 µg + Chitosan/CpG 100% Encapsulated | 34,057 | 64,456 | 2048 |
| 5 | PLG/Men B 10 µg + Chitosan/CpG 50% Encapsulated | 25,204 | 16,315 | 4096 |

Although preferred embodiments of the subject invention have been described in some detail, it is understood that obvious variations can be made without departing from the spirit and the scope of the invention.

3. The immunogenic composition of claim 1, wherein said cationic polysaccharide comprises D-glucosamine monomer units.

4. The immunogenic composition of claim 1, wherein said cationic polysaccharide comprises a combination of D-glucosamine and N-acetyl-D-glucosamine monomer units.

5. The immunogenic composition of claim 1, wherein said cationic polysaccharide comprises a polymer chain that comprises randomly distributed β-(1-4)-linked D-glucosamine and N-acetyl-D-glucosamine monomer units.

6. The immunogenic composition of claim 1, wherein said cationic polysaccharide comprises chitosan.

7. The immunogenic composition of claim 1, wherein said cationic polysaccharide has a molecular weight ranging from 100,000 g/mol to 1,250,000 g/mol.

8. The immunogenic composition of claim 1, wherein said cationic polysaccharide has a pKa ranging from 6.0 to 7.0.

9. The immunogenic composition of claim 1, wherein the weight ratio of said cationic polysaccharide to said immunological species ranges from 0.0001:1 to 0.01:1.

10. The immunogenic composition of claim 1, wherein the immunological species is a negatively charged immunological adjuvant.

11. The immunogenic composition of claim 1, wherein the immunological species is a CpG oligonucleotide.

12. The immunogenic composition of claim 1, wherein said composition comprises a synthetic biodegradable polymer.

13. The immunogenic composition of claim 1, wherein said composition comprises a biodegradable polymer selected from a poly(α-hydroxy acid), a polyhydroxy butyric acid, a polylactone, a polyorthoester, a polyanhydride, a polycyanoacrylate, a tyrosine-derived polycarbonate, a tyrosine-derived polyester-amide, and combinations thereof.

What is claimed:

1. An immunogenic microparticle composition comprising polymer microparticles comprising a biodegradable polymer, said microparticle composition further comprising a cationic polysaccharide and a negatively charged immunological species selected from an antigen, an immunological adjuvant and combinations thereof, wherein a complex comprising said immunological species and said cationic polysaccharide is entrapped within at least a portion of said microparticles, and wherein the weight ratio of said cationic polysaccharide to said biodegradable polymer ranges from 0.000005:1 to 0.005:1.

2. The immunogenic composition of claim 1, wherein said cationic polysaccharide comprises an amine-substituted cationic polysaccharide.

14. The immunogenic composition of claim 1, wherein said biodegradable polymer comprises a poly(α-hydroxy acid).

15. The immunogenic composition of claim 1, wherein said biodegradable polymer comprises a poly(α-hydroxy acid) that is selected from poly(lactide), poly(glycolide), poly(lactide-co-glycolide) and combinations thereof.

16. The immunogenic composition of claim 1, wherein said biodegradable polymer comprises a poly(lactide-co-glycolide) having a lactide:glycolide molar ratio ranging from 40:60 to 60:40.

17. The immunogenic composition of claim 16, wherein said composition comprises at least 90 wt % biodegradable polymer.

18. The immunogenic composition of claim 1 wherein the D(v,0.5) particle size of said microparticles ranges from 0.1 to 50 microns.

19. The immunogenic composition of claim 1, wherein the D(v,0.5) particle size of said microparticles ranges from 0.5 to 10 microns.

20. The immunogenic composition of claim 1, wherein said immunological species comprises an antigen.

21. The immunogenic composition of claim 20, wherein the antigen is a polypeptide-containing antigen.

22. The immunogenic composition of claim 20, wherein the antigen is a polynucleotide-containing antigen.

23. The immunogenic composition of claim 20, wherein the antigen is a saccharide-containing antigen.

24. The immunogenic composition of claim 20, wherein the antigen is derived from a tumor cell.

25. The immunogenic composition of claim 20, wherein the antigen is derived from a pathogenic organism.

26. The immunogenic composition of claim 25, wherein the pathogenic organism is selected from a virus, a bacterium, a fungus and a parasite.

27. The immunogenic composition of claim 25, wherein the pathogenic organism is selected from HIV, hepatitis B virus, hepatitis C virus, meningitis B, *Haemophilus influenza* type B, pertussis, diphtheria, tetanus, and influenza A virus.

28. The immunogenic composition of claim 1, wherein said immunological species comprises an immunological adjuvant.

29. The immunogenic composition of claim 1, wherein said immunological species comprises an immunological adjuvant selected from CpG oligonucleotides and Monophosphoryl lipid A analogs.

30. A vaccine comprising the immunogenic composition of claim 1.

31. The immunogenic microparticle composition of claim 1, wherein said microparticles are formed by a process that comprises: (a) emulsifying an organic phase comprising said biodegradable polymer and an organic solvent with a first aqueous phase comprising water and said complex of said cationic polysaccharide and said immunological species, thereby forming a water-in-oil emulsion; (b) emulsifying a second aqueous phase comprising a surfactant and water with the emulsion formed in step (a) to form a water-in-oil-in-water emulsion; and (c) removing the organic solvent from the water-in-oil-in-water emulsion.

32. The immunogenic microparticle composition of claim 31, wherein said immunological species is an immunological adjuvant.

33. The immunogenic microparticle composition of claim 32, wherein the surfactant is an anionic surfactant.

34. The immunogenic microparticle composition of claim 33, further comprising an adsorbed polypeptide-containing antigen.

35. The immunogenic microparticle composition of claim 1, where a portion of the immunological species is neither adsorbed to nor encapsulated within the microparticles.

36. The immunogenic microparticle composition of claim 1, further comprising microparticles with adsorbed immunological species.

37. An immunogenic microparticle composition comprising polymer microparticles comprising a biodegradable polymer, said microparticle composition further comprising a cationic polysaccharide and an immunological species selected from an antigen, an immunological adjuvant and combinations thereof, wherein said immunological species is adsorbed to at least a portion of said microparticles, wherein said immunological species is not entrapped within said microparticles, and wherein the weight ratio of said cationic polysaccharide to said biodegradable polymer ranges from 0.0005:1 to 0.05:1.

38. The immunogenic composition of claim 37, wherein said composition is a lyophilized composition.

39. The immunogenic composition of claim 38, wherein upon reconstitution of 10 mg of the lyophilized composition of claim 10 in 1 ml water, the resulting suspension exhibits a release profile wherein 10% or more of the total amount of adsorbed immunological adjuvant is released from the microparticles beyond 15 days after reconstitution.

40. The immunogenic composition of claim 37, wherein the weight ratio of said cationic polysaccharide to said biodegradable polymer ranges from 0.0025:1 to 0.01:1.

41. The immunogenic composition of claim 37, wherein the weight ratio of said immunological species to said biodegradable polymer ranges from 0.0005:1 to 0.05:1.

42. The immunogenic composition of claim 37, wherein the weight ratio of said immunological species to said biodegradable polymer ranges from 0.001:1 to 0.025:1.

43. A kit comprising a first container comprising the lyophilized composition of claim 38.

44. The kit of claim 43, further comprising a second container comprising a sterile liquid medium useful to resuspend the lyophilized composition in the first container.

45. The kit of claim 43, further comprising a syringe.

46. An immunogenic microparticle composition comprising polymer microparticles comprising a biodegradable polymer, said microparticle composition further comprising a cationic polysaccharide, an antigen and an immunological adjuvant, wherein said antigen is adsorbed to at least a portion of said microparticles and is not entrapped within said microparticles, and wherein said immunological adjuvant is entrapped within at least a portion of said microparticles, and wherein the weight ratio of said cationic polysaccharide to said biodegradable polymer ranges from 0.000005:1 to 0.005:1.

47. The immunogenic microparticle composition of claim 46, wherein said antigen is adsorbed to and said immunological adjuvant is entrapped within the same microparticles.

48. The immunogenic microparticle composition of claim 46, wherein said antigen is adsorbed to and said immunological adjuvant is entrapped within different microparticles.

49. The immunogenic microparticle composition of claim 46, wherein a complex comprising said immunological adjuvant and said cationic polysaccharide is entrapped within at least a portion of said microparticles, and wherein said immunological adjuvant is a negatively charged immunological adjuvant.

50. The immunogenic microparticle composition of claim 49, wherein said antigen is a polypeptide-containing antigen and wherein at least a portion of said polymer microparticles further comprise an anionic surfactant.

51. The immunogenic microparticle composition of claim 49, wherein said immunological adjuvant is a negatively charged immunological adjuvant.

52. The immunogenic microparticle composition of claim 51, wherein the cationic polysaccharide comprises D-glucosamine monomer units.

53. The immunogenic microparticle composition of claim 52, wherein the biodegradable polymer comprises a poly($\alpha$-hydroxy acid) that is selected from poly(lactide), poly(glycolide), poly(lactide-co-glycolide) and combinations thereof.

54. The immunogenic microparticle composition of claim 53, wherein said negatively charged immunological adjuvant is selected from CpG oligonucleotides and Monophosphoryl lipid A analogs.

55. A method of producing a microparticle composition in accordance with claim 1 comprising:

(a) emulsifying an organic phase comprising the biodegradable polymer and an organic solvent with a first aqueous phase comprising water, the cationic polysaccharide and the immunological species, thereby forming a water-in-oil emulsion; and
(b) emulsifying a second aqueous phase comprising a surfactant and water with the emulsion formed in step (a) to form the water-in-oil-in-water emulsion; and
(c) removing the organic solvent from the water-in-oil-in-water emulsion.

56. The method of claim 55, wherein the surfactant is an anionic surfactant.

57. A method of stimulating an immune response in a vertebrate host animal, comprising administering to the host animal the immunogenic composition of claim 1.

58. The method of claim 57, wherein the vertebrate host animal is human.

59. A method of immunizing a vertebrate host animal against a pathogenic organism or a tumor comprising administering to the animal the composition of claim 1.

60. The method of claim 59, wherein the vertebrate host animal is human.

61. A method of producing a microparticle composition in accordance with claim 37 comprising: (a) providing an emulsion comprising water, organic solvent, a biodegradable polymer and a cationic polysaccharide; (b) removing the organic solvent from the emulsion to form microparticles; and (c) adsorbing the immunological species to the microparticles.

62. The method of claim 61, wherein said microparticles have a zeta potential ranging from 25 to 100 mV at pH ranging from 5 to 6.5 prior to adsorption of said antigen.

63. The method of claim 61, wherein said emulsion is a water-in-oil-in-water emulsion.

64. The method of claim 63, wherein the water-in-oil-in-water emulsion is formed by a process that comprises:
(a) emulsifying an organic phase comprising the biodegradable polymer and the organic solvent with a first aqueous phase comprising water, thereby forming a water-in-oil emulsion; and
(b) emulsifying a second aqueous phase comprising the cationic polysaccharide and water with the emulsion formed in step (a) to form the water-in-oil-in-water emulsion.

65. The method of claim 64, wherein the pH of the second aqueous phase ranges from 4.5 to 6.0.

* * * * *

SEQUENCE LISTING

<160> NUMBER OF SEQ ID NOS: 1

<210> SEQ ID NO 1
<211> LENGTH: 19
<212> TYPE: DNA
<213> ORGANISM: Artificial
<220> FEATURE:
<223> OTHER INFORMATION: Artifical Sequence is synthesized

<400> SEQUENCE: 1
tccatgacgt tcctgacgt                                            19